US009289177B2

(12) United States Patent
Kassim et al.

(10) Patent No.: US 9,289,177 B2
(45) Date of Patent: Mar. 22, 2016

(54) SENSING DEVICE, A METHOD OF PREPARING A SENSING DEVICE AND A PERSONAL MOBILE SENSING SYSTEM

(75) Inventors: Md. Irwan bin Md. Kassim, Synapse (SG); Mohamad Sulhede Bin Samsudin, Synapse (SG)

(73) Assignee: NITTO DENKO CORPORATION, Osaka (JP)

( * ) Notice: Subject to any disclaimer, the term of this patent is extended or adjusted under 35 U.S.C. 154(b) by 307 days.

(21) Appl. No.: 13/884,537

(22) PCT Filed: Jan. 5, 2012

(86) PCT No.: PCT/SG2012/000007
§ 371 (c)(1),
(2), (4) Date: Jul. 25, 2013

(87) PCT Pub. No.: WO2012/099539
PCT Pub. Date: Jul. 26, 2012

(65) Prior Publication Data
US 2013/0296714 A1 Nov. 7, 2013

Related U.S. Application Data

(63) Continuation-in-part of application No. 13/010,705, filed on Jan. 20, 2011, now Pat. No. 8,761,853.

(51) Int. Cl.
*A61B 5/1455* (2006.01)
*A61B 5/00* (2006.01)
(Continued)

(52) U.S. Cl.
CPC ............ *A61B 5/6898* (2013.01); *A61B 5/0059* (2013.01); *A61B 5/0295* (2013.01); *G01N 21/3151* (2013.01); *A61B 5/021* (2013.01);
(Continued)

(58) Field of Classification Search
CPC ............ A61B 5/1455; A61B 5/14551; A61B 5/14552; A61B 5/6898; A61B 2562/0247
See application file for complete search history.

(56) References Cited

U.S. PATENT DOCUMENTS 7,251,513 B2 * 7/2007 Kondoh et al. ............... 600/310
7,483,731 B2 * 1/2009 Hoarau et al. ............... 600/344
(Continued)

FOREIGN PATENT DOCUMENTS

CN 1942754 A 4/2007
JP 2004-358022 A 12/2004
(Continued)

OTHER PUBLICATIONS

International Search Report issued in PCT/SG2012/000007 mailed Mar. 19, 2012 (2 pages).
(Continued)

*Primary Examiner* — Eric Winakur
(74) *Attorney, Agent, or Firm* — Osha Liang LLP

(57) ABSTRACT

There is provided a sensing device comprising an electromagnetic wave emitter for emitting electromagnetic waves to a surface; an electromagnetic wave detector for detecting the emitted electromagnetic waves that are reflected from the surface; and a force transmitting member configured to transmit a force applied thereto for detection, wherein the force transmitting member is positioned relative to the electromagnetic wave emitter and electromagnetic wave detector to substantially prevent waves emitted by the electromagnetic wave emitter from travelling directly to the electromagnetic wave detector.

24 Claims, 28 Drawing Sheets

(51) Int. Cl.
*A61B 5/0295* (2006.01)
*G01N 21/31* (2006.01)
*A61B 5/021* (2006.01)

(52) U.S. Cl.
CPC ........... *A61B5/14551* (2013.01); *A61B 5/7435* (2013.01); *A61B 2562/0247* (2013.01); *A61B 2562/0252* (2013.01); *G01N 2021/3144* (2013.01)

(56) References Cited

U.S. PATENT DOCUMENTS

| 8,306,593 | B2* | 11/2012 | Hwang et al. ................ 600/316 |
| 8,352,004 | B2* | 1/2013 | Mannheimer et al. ........ 600/310 |
| 2001/0000790 | A1 | 5/2001 | Delonzor et al. |
| 2008/0265145 | A1 | 10/2008 | Uchida |
| 2010/0249554 | A1 | 9/2010 | McKenna et al. |
| 2010/0298678 | A1* | 11/2010 | Klomhaus .................... 600/344 |
| 2010/0305418 | A1 | 12/2010 | Deliwala |
| 2011/0065482 | A1 | 3/2011 | Koide et al. |

FOREIGN PATENT DOCUMENTS

| JP | 2006-011711 A | 1/2006 |
| JP | 2009-201895 A | 9/2009 |
| WO | 2009/136341 A2 | 11/2009 |
| WO | 2009/139244 A1 | 11/2009 |

OTHER PUBLICATIONS

International Preliminary Report on Patentability issued in PCT/SG2012/000007 mailed Aug. 21, 2012 (13 pages).
Office Action issued in counterpart Chinese Patent Application No. 201280003878.X mailed on Oct. 29, 2014 (17 pages).
Office Action issued in counterpart Chinese Patent Application No. 201280003878.X dated Dec. 29, 2015 (12 pages).

* cited by examiner

SENSING DEVICE, A METHOD OF PREPARING A SENSING DEVICE AND A PERSONAL MOBILE SENSING SYSTEM

CROSS-REFERENCE TO RELATED APPLICATIONS

This application is a national phase application of PCT/SG2012/000007 (hereinafter "international application"), filed on Jan. 5, 2012. The international application claims priority to U.S. patent application Ser. No. 13/010,705 (hereinafter "priority application"), filed on Jan. 20, 2011. The priority application is hereby incorporated by reference in its entirety.

TECHNICAL FIELD

The present invention relates to sensing devices, in particular devices for non-invasive sensing of physiological measurements, including the detection of a photoplethysmography (PPG) signal from a user.

BACKGROUND

Various types of sensing devices that sense physiological characteristics are currently available. Reflectance-based sensing devices that detect emitted waves which are reflected off the surface of a living tissue in order to obtain a physiological measurement may be particularly useful for detection of certain physiological characteristics.

For example, reflectance-based sensing devices may be used to detect photoplethysmography (PPG) signals. PPG is an optical measurement technique used to detect blood volume changes in the microvascular bed of living tissue, typically by detecting light transmitted through the ear lobe or fingertip. As arterial pulsations enter the capillary bed, changes in the volume of the blood vessels or characteristics of the blood itself modify the optical properties of the capillary bed. The PPG signal is used to measure saturation of peripheral oxygen (SpO2), which is an estimation of the level of oxygen saturation in a fluid, such as blood. The PPG signal can also be used to measure blood pressure.

The majority of PPG devices currently available, rely on simple thresholding, or peak detection algorithms, to find the principal peaks in a detected signal. However, these methods are unreliable when the detected signal is less than ideal. Particular problems may be encountered when the baseline of the AC signal component becomes noisy or complex, as can occur even with mild movement artifacts. For many reflectance-based PPG devices, the majority of the noise may also arise due to direct transmittance of waves from the wave source to the waves detector (i.e. non-reflected waves).

In view of the above, there exists a need for a sensing device that overcomes or ameliorates at least some of the above mentioned problems. There is also a need to provide a reflectance-based sensing device which ensures that its wave detector is effectively shielded from the wave emitting source to reduce noise in the readings.

SUMMARY

According to one aspect, there is provided a sensing device comprising an electromagnetic wave emitter for emitting electromagnetic waves to a surface; an electromagnetic wave detector for detecting the emitted electromagnetic waves that are reflected from the surface; and a force transmitting member configured to transmit a force applied thereto for detection, wherein the force transmitting member is positioned relative to the electromagnetic wave emitter and electromagnetic wave detector to substantially prevent electromagnetic waves emitted by the wave emitter from travelling directly to the wave detector. Advantageously, the sensing device is capable of detecting reflected light signals as well as transmitting a user applied force for detection. Even more advantageously, the configuration and positioning of the force transmitting member reduce noise in the detected signals without the need of an additional shading/shielding wall to substantially prevent electromagnetic waves emitted by the electromagnetic wave emitter from travelling directly to the electromagnetic wave detector. Due to the absence of an additional shading/shielding wall, the sensing device can be more easily compacted, thereby advantageously increasing user portability. In one embodiment, the force transmitting member is disposed between the electromagnetic wave detector and electromagnetic wave emitter to advantageously remove a direct line of sight between the electromagnetic wave detector and electromagnetic wave emitter.

For PPG devices which require a force to be exerted onto the detected surface, a specific optimum force (zero transmural pressure) is required to acquire the best PPG signal for each individual. Some individuals, for example those with superficial capillaries, may not need to exert too much force in order to achieve the optimal pressure for the best PPG signal from the detected surface. For this group of people, exerting more force may excessively compress their surface capillaries resulting in little or no detected PPG signal. Thus, the inventors have discovered that a force detector may be implemented on such PPG devices to provide feedback on the optimal pressure that should be exerted in order to improve the quality of the detected signal. In such devices, the force transmitting member can not only block of stray electromagnetic wave from the wave emitter but can also advantageously be used to transmit exerted force to the force detector without the need to introduce a separate member to solely transmit the exerted force.

In one embodiment, the force transmitting member is configured to be displaced from a starting position upon application of the force to said member. Advantageously, the amount of displacement may be used to correlate to the force applied and allows the effective force detection.

In one embodiment, the sensing device further comprises a force detector coupled to the force transmitting member for detecting the force transmitted by the force transmitting member. Advantageously, the force detector provides in situ force detection.

In one embodiment, the force detector comprises a microelectromechanical system (MEMs). Advantageously, the force detector can be easily installed in the sensing device without adversely compromising on the overall compactness or size of the sensing device. In one embodiment, the force detector comprises a piezo-based sensor. The piezo-based sensor can be selected from the group consisting of a piezoelectric based sensor, a piezoresistive based sensor, and a piezocapacitive based sensor. In such embodiments, little or substantially no displacement or deformation of the force transmitting member may be required to produce an accurate reading of the applied force. This again beneficially reduces the amount of space within the sensing device required for allowing any displacement or deformation to take place. Even more advantageously, as the moving parts involved are reduced, there may be less wear and tear of the internal components, thereby increasing the life span of the device. The piezo-based sensor can be provided as a flexible printed circuit.

In one embodiment the wave emitter comprises a light emitting diode. Advantageously, the small size of the light emitting diode contributes to the overall compactness of sensing device. In one embodiment, the electromagnetic wave detector comprises a photo detector.

In one embodiment, the surface comprises a surface portion of a user for measurement. This beneficially allows the sensing device to be used as a medical sensing device to acquire signals pertinent to physiological measurements.

In one embodiment, the force transmitting member is elongate in shape. Advantageously, the elongate shape is of a height that is capable of substantially preventing waves emitted from the wave emitter to travel directly to the wave detector and a width that does not unnecessarily increase the space required for accommodating the member.

In one embodiment, the sensing device comprises a resilient means coupled to the force transmitting member for returning the force transmitting member to the starting position after an applied force is removed from the force displaceable member. This allows a new force reading to be taken whenever a force is removed.

In one embodiment, the electromagnetic wave emitter and electromagnetic wave detector are disposed on substantially the same plane. This may advantageously reduce the amount of electromagnetic waves that are directly transmitted from the electromagnetic wave emitter to the wave detector. The electromagnetic wave emitter and electromagnetic wave detector may be disposed on a same substrate. Accordingly, the number of substrates used may be reduced.

In one embodiment, the sensing device further comprises a feedback unit coupled to the force detector, the feedback unit being configured to correlate the quality of the detected wave with the amount of force applied to the force transmitting member and provide feedback related to the correlation. The feedback unit may provide useful information to the user such as whether to reduce or increase the pressure of the detected surface.

In one embodiment, the sensing device is capable of detecting photoplethysmography signals. Several useful physiological data can be beneficially derived from the photoplethysmograph signals.

In one embodiment, the sensing device further comprises a housing for housing the electromagnetic wave emitter, electromagnetic wave detector and force transmitting member, wherein the housing is adapted to provide structural rigidity to the sensing device. Advantageously, the house provides a protective covering for the sensitive components of the sensing device.

According to another aspect, there is provided a method for preparing a sensing device comprising providing an electromagnetic wave emitter for emitting electromagnetic waves to a surface; providing an electromagnetic wave detector for detecting the emitted electromagnetic waves that are reflected from the surface; positioning a force transmitting member relative to the electromagnetic wave emitter and electromagnetic wave detector for substantially preventing electromagnetic waves emitted by the electromagnetic wave emitter from travelling directly to the electromagnetic wave detector, wherein the force displaceable member is configured to transmit a force applied thereto for detection. The force transmitting member may be configured to be displaced from a starting position upon application of a force to said member.

According to another aspect, there is provided a personal mobile sensing system comprising a sensing device, the sensing device comprising an electromagnetic wave emitter for emitting electromagnetic waves to a surface, an electromagnetic wave detector for detecting the emitted electromagnetic waves that are reflected from the surface, and a force transmitting member configured to transmit a force applied thereto for detection, wherein the force transmitting member is positioned relative to the electromagnetic wave emitter and electromagnetic wave detector to substantially prevent electromagnetic waves emitted by the electromagnetic wave emitter from travelling directly to the electromagnetic wave detector. The force transmitting member may be configured to be displaced from a starting position upon application of the force to said member. The force transmitting member may be disposed between the electromagnetic wave emitter and electromagnetic wave detector. The sensing device may further comprise a force detector coupled to the force transmitting member for detecting the force transmitted by the force transmitting member. The force detector may comprise a micro-electromechanical system (MEMs). The piezo-based sensor can be selected from the group consisting of a piezoelectric based sensor, a piezoresistive based sensor, and a piezocapacitive based sensor. The piezo-based sensor can be provided as a flexible printed circuit. The surface may comprise a surface portion of a user for measurement. The electromagnetic wave emitter and electromagnetic wave detector may be disposed on substantially the same plane. The personal mobile processing device may further comprise a feedback unit coupled to the force detector, the feedback unit being configured to correlate the quality of the detected electromagnetic wave with the amount of force applied to the force transmitting member and provide feedback related to the correlation. The sensing device may be capable of detecting photoplethysmography signals. The sensing device may be coupled to the personal mobile processing device in a cableless configuration.

DESCRIPTION OF OPTIONAL EMBODIMENTS

Non-limiting example embodiments of a sensing device, a method for preparing a sensing device and a personal mobile sensing system are disclosed in the following paragraphs.

There is provided a sensing device comprising an electromagnetic wave emitter for emitting electromagnetic waves to a surface; an electromagnetic wave detector for detecting the emitted electromagnetic waves that are reflected from the surface; and a force transmitting member configured to transmit a force applied thereto for detection, wherein the force transmitting member is positioned relative to the electromagnetic wave emitter and electromagnetic wave detector to substantially prevent electromagnetic waves emitted by the electromagnetic wave emitter from travelling directly to the electromagnetic wave detector.

Preferably, the sensing device is a reflectance-based sensing device which relies on the detection of reflected waves to give a useful reading or measurement. In one embodiment, the sensing device is capable of working as both a reflectance-based sensing device and a transmittance-based sensing device and is capable of detection of reflected waves or transmitted waves to give a useful reading or measurement. In some embodiments, the sensing device is an optical sensing device. The sensing device may also be capable of sensing a plurality of different parameters, for example, the sensing device may be capable of sensing pressure or force applied to a surface as well as light reflected off the surface. In certain embodiments, the sensing device is a medical sensing device that is configured to sense a parameter that is useful to measure a physiological characteristic.

The electromagnetic wave emitter may be replaced by other kinds of wave emitters such as sound wave emitters. Exemplary sound waves include but are not limited to ultrasound waves and sound waves which have wavelengths that are within the human audible hearing range. Preferably, the wave emitter of the sensing device is an electromagnetic wave emitter. Exemplary electromagnetic waves include but are not limited to X-rays, visible light rays and infra-red rays. In one embodiment, the wave emitter comprises a light emitting diode.

The electromagnetic wave detector may be replaced by other kinds of wave detectors, such as sound wave detectors. Exemplary sound waves include but are not limited to ultrasound waves and sound waves which have wavelengths that are within the human audible hearing range. Preferably, the wave detector of the sensing device is an electromagnetic wave detector. Exemplary electromagnetic waves include but are not limited to X-rays, visible light rays and infra-red rays. In one embodiment, the wave detector comprises a photo detector.

In one embodiment, the base of the wave emitter and the base of the wave detector are disposed on substantially the same plane. In other embodiments, the base of the wave emitter and the base of the wave detector may be disposed on different planes but which are substantially parallel to each other. The planes disclosed in the above embodiments may be planes that are substantially parallel to the base of the sensing device. In one embodiment, the wave emitter and wave detector are disposed on a same substrate. In another embodiment, the wave emitter and the wave detector are disposed on different substrates but are disposed on substantially the same plane. In one embodiment, the emission surface of the wave emitter and the detection surface of the wave detector are on substantially parallel planes. The emission surface of the wave emitter and the detection surface of the wave detector may also be on substantially the same plane.

The force transmitting member of the sensing device may be configured to be displaced from a default starting position upon application of the force to said member. In one embodiment, the force transmitting member displaces relative to at least one of the wave detector and wave emitter. Preferably, the force transmitting member is still capable of substantially preventing waves emitted by the wave emitter from travelling directly to the wave detector throughout the application of force on the force transmitting member, where the force transmitting member is displaced from the starting point to its maximum displacement distance from the starting position. In another embodiment, the force transmitting member is not substantially displaced or deformed, but merely allows an applied force to be transmitted to a sensor beneath the wave detector and emitter. The force transmitting member may be disposed between the wave emitter and the wave detector for substantially preventing waves emitted by the wave emitter from travelling directly to the wave detector. The force transmitting member may also have a configuration that substantially prevents waves emitted from the wave emitter to travel directly to the wave detector. Such configuration may be a structural or shape configuration. For example, the force transmitting member may have a portion extending between the wave emitter and wave detector. Accordingly, in some embodiments, the force transmitting member is disposed in positions other than between the wave emitter and wave detector but has a configuration (for eg. a structure or shape) that is still capable of substantially preventing waves emitted from the wave emitter to travel directly to the wave detector. The force transmitting member may serve to remove a direct line of sight from the wave detector to the wave emitter. In a preferred embodiment, the force transmitting member is elongate in shape. The force transmitting member may also be a columnar structure or a cylindrical structure and may have a solid or hollow core without compromising on its ability to substantially prevent waves emitted by the wave emitter from travelling directly to the wave detector. The force transmitting member may comprise an overhead component extended outwards for increasing the surface area available to substantially prevent waves emitted from the wave emitter to travel directly to the wave detector. In one embodiment, the force transmitting member has a longitudinal cross section that resembles a "T" or an "i" shape. Preferably, the force transmitting member is made of a material that is substantially impermeable to waves emitted by the wave emitter, such that the waves emitted from the wave emitter is substantially prevented from travelling directly to the wave detector. In some embodiments, the force transmitting member is coated with a coating layer that is substantially impermeable to waves emitted by the wave emitter, such that the waves emitted from the wave emitter is substantially prevented from travelling directly to the wave detector. In one embodiment, the force transmitting member is made of a material that is sufficiently rigid to be able to transmit a force applied thereto without an appreciable deformation. In one embodiment the force transmitting member is made of polymers. The polymers may be selected from a group consisting of a polyvinyl resin, a vinyl acetate-ethylene copolymer, a vinyl polymer, an acrylic resin, a cellulose derivative and a polyolefin. In particular, the polymers may be selected from the group consisting of poly(ethyl vinyl acetate), polyethylene, polypropylene, polystyrene polyamide. In one embodiment, the material of the force transmitting member comprises at least one of ABS (Acrylonitrile butadiene styrene) and PC (Polycarbonate). Preferably, the force transmitting member is substantially opaque. Alternatively, the force transmitting member may be translucent as long as the amount of light allowed to pass through does not substantially negatively affect the readings of the wave detector. The force transmitting member may be manufactured by plastics molding, such as cold molding, compression molding, injection molding etc. In some embodiments, the force transmitting member is substantially non-deformable. In alternative embodiments, the force transmitting member is deformable when a force is applied to it. Accordingly, the detection of the applied force may be based on the degree of deformation experienced by the force transmitting member. In such cases, it is preferable that the force transmitting member is still capable of substantially preventing waves emitted by the wave emitter from travelling directly to the wave detector throughout its deformation when a force is applied to it.

The sensing device may further comprise a resilient means coupled to the force transmitting member for returning the force transmitting member to the starting position after an applied force is removed from the force displaceable member. Such resilient means may comprise a spring or a material having sufficient flexural strength to flex when a bending force is applied and to substantially return to its original shape upon removal of the force.

In one embodiment, the sensing device disclosed herein further comprises a force detector or pressure sensor (the terms may be used interchangeably herein) coupled to the force transmitting member for detecting the force transmitted by the force transmitting member. Via the force transmitting member, the force detector or pressure sensor can detect the amount of pressure that has been applied by a body part of the user, such as a finger. The force detector may comprise a microelectromechanical system (MEMs). In one embodiment, the force detector comprises a piezo-based sensor which measures the force applied to a material by correlating based on physical and/or electrical property changes of the material due to mechanical stress. Such material can include but is not limited to crystals, ceramics or semiconductors. The electrical property changes can include but are not limited to changes in conductivity, resistivity, resistance, capacitance and/or generated electric charge of the material, The piezo-based sensor can selected from the group consisting of a piezoelectric based sensor, a piezoresistive based sensor, a piezocapacitive based sensor or the like. Accordingly, the force detector or pressure sensor may be in the form of a thin film flexible printed circuit implementing the piezo-based sensor. The components of the force detector or pressure sensor may be implemented in the form of a Wheatstone bridge circuit/configuration. In exemplary embodiments, the force transmitting member is rested on the force sensor and transmits the force applied thereto to the force sensor without substantial displacement or deformation of the force transmitting member. In such embodiments, while some displacement or deformation may be present (for e.g. in a microscale), these displacements or deformations may not be appreciable to the naked eye. In some embodiments, the transmitting member is an integral part of the force sensor. The force sensor and the force transmitting member may form a single body.

In alternative embodiments, the force detector or pressure sensor can detect the force transmitted by mechanical means, for example by an appreciable amount of displacement or by electrical means, for example by change of resistance. When the force transmitting member is deformable upon application of a force thereon, the force detector or pressure sensor may detect the applied force based on the degree of deformation experienced by the force transmitting member. In other embodiments, other force measuring device that is capable of sensing an applied contact force may also be used. In some embodiments, the force detector or pressure sensor is positioned below the wave sensor and wave detector.

The surface which reflects the waves to the wave detector for detection may comprise a surface portion of a user for measurement. The surface portion may be a living tissue such as a surface of a finger, surface of an ear lobe or any part of the body has the desired measurable physiological characteristics. In one embodiment, the sensing device is capable of detecting photoplethysmography (PPG) signals from the surface.

In one embodiment, the disclosed sensing device comprises a feedback unit coupled to the force detector, the feedback unit being configured to correlate the quality of the detected wave with the amount of force applied to the force transmitting member and provide feedback related to the correlation. The feedback unit may be a unit detachable from the sensing device. In some embodiments, the feedback unit is a unit integrated with the sensing device or vice versa. The feedback unit may be a component of a personal mobile processing device. In some embodiments, when the feedback unit is a detachable unit, the largest dimension of the sensing device is smaller than the largest dimension of the detachable feedback unit.

Preferably, the disclosed sensing device further comprises a housing for housing the wave emitter, wave detector and force transmitting member, wherein the housing is adapted to provide structural rigidity to the sensing device. The housing may also house the additional components that are described above. In one embodiment, the housing is made of polymers. The polymers may be selected from a group consisting of a polyvinyl resin, a vinyl acetate-ethylene copolymer, a vinyl polymer, an acrylic resin, a cellulose derivative and a polyolefin. In particular, the polymers may be selected from the group consisting of poly(ethyl vinyl acetate), polyethylene, polypropylene, polystyrene and polyamide. In one embodiment, the material of the housing comprises at least one of ABS (Acrylonitrile butadiene styrene) and PC (Polycarbonate). The housing may be manufactured by plastics molding, such as cold molding, compression molding, injection molding etc.

The sensing device may further comprise a cantilever means coupled to said force transmitting member for transmitting an exerted force by a cantilever moment to the force transmitting member. The cantilever means may be a beam-like structure supported by at least one fulcrum. In one embodiment, when in use, the fulcrum is disposed at one end of the beam-like structure. The cantilever means may also comprise a mating means that is capable of mating with a complementary matching means of a housing. The mating means of the cantilever means may be any physical feature that is capable of mating with the matching means of the housing so that the cantilever means can fit snugly within the housing. Likewise, the matching means of the housing may be any physical feature that is capable of mating with the mating means of the cantilever means to provide secure engagement therewith. In one embodiment, the mating means comprises one or more features selected from the group consisting of a protrusion, projection, abutment, extension and the like, while the matching means comprises one or more features selected from the group consisting of a hole, slot, depression, recess, opening, aperture and the like. In another embodiment, the matching means comprises one or more features selected from the group consisting of a protrusion, projection, abutment, extension and the like, while the mating means comprises one or more features selected from the group consisting of a hole, slot, depression, recess, opening, aperture and the like. Preferably, both the mating means and matching means are stepped structures that are complementary to each other. In other embodiments, the cantilever means may be part of the force transmitting member and vice versa such that both the cantilever means and the force transmitting member form a single unitary structure.

The sensing device may also further comprise a coupling member for coupling to an external processing device which is configured to process the signals from the sensing device. The coupling member may comprise a data communication port. Examples of possible data communication ports include but are not limited to a Universal Serial Bus (USB) port, an IEEE 1384 port, a serial port, a parallel port, a Personal Computer Memory Card International Association (PCM-CIA) port, an Inter-Integrated Circuit (I2C) port, a Small Computer System Interface (SCSI) port, an optical port, a coaxial port, a Registered Jack 45 (RJ45) port and a Registered Jack 11 (RJ11) port, a 30 pin connector/connection such as that used in the Apple® iPhone® (Apple Computer, Inc., Cupertino, Calif.) or Samsung™ mobile devices.

In one embodiment, the sensing device further comprises a measurement surface for receiving a surface portion of the user. The measurement surface can be an orientation-free surface which is not limited to a single orientation at which the surface must be placed. For example, the orientation-free measurement surface does not require the surface to be placed in any particular orientation, as long as the surface in contact with the orientation-free measurement surface, is capable of reflecting the emitted waves towards the wave detector. In one embodiment, the orientation-free measurement surface is not a clip or a cuff, which requires the surface to be detected, for example a finger, to be placed in a particular orientation. In some embodiments, the orientation-free measurement surface does not comprise any mechanical or adhesive means to urge the measurement surface towards the surface that is to be detected. For example, in some embodiments, the orientation-free measurement surface does not comprise an adhesive patch, a cuff or a clip to provide an inherent compressive or adhesive force to urge the measurement surface towards the surface that is to be detected. In some embodiments, the orientation-free measurement surface is capable of advantageously detecting a 2-dimensional surface as compared to a clip or cuff, which requires that the portion of the user to be detected to be 3-dimensional, in order to ensure sufficient engagement with the clip or the cuff for detection purposes. The measurement surface may have a surface area no larger than 60 cm$^2$, no larger than 50 cm$^2$, no larger than 40 cm$^2$, no larger than 30 cm$^2$, no larger than 25 cm$^2$, no larger than 20 cm$^2$, no larger than 15 cm$^2$, or no larger than 10 cm$^2$.

Preferably, the contact of the orientation-free measurement surface with a surface portion of a user that is to be detected is carried out by a force applied by the user.

There is also provided a method for preparing a sensing device comprising providing a wave emitter for emitting waves to a surface; providing a wave detector for detecting the emitted waves that are reflected from the surface emitting waves to a surface from a wave emitter; positioning a force transmitting member relative to the wave emitter and wave detector for substantially preventing waves emitted by the wave emitter from travelling directly to the wave detector, wherein the force transmitting member is configured to transmit a force applied thereto for detection. In exemplary embodiments, the force transmitting member is rested on a force sensor and transmits the force applied thereto to the force sensor without substantial displacement or deformation of the force transmitting member. In such embodiments, while some displacement or deformation may be present (for e.g. in a microscale), these displacements or deformations may not be appreciable to the naked eye. In alternative embodiments, the force transmitting member is configured to be displaced from a starting position upon application of a force to said member. The method may further comprise housing the wave emitter, wave detector and force transmitting member in a housing. The sensing device and its components disclosed in the method may be similar to those described in paragraphs above.

There is also provided a personal mobile sensing system comprising a sensing device and a personal mobile processing device for coupling to the sensing device to process a signal obtained from said sensing device. The sensing device and its components disclosed in the system may be similar to those described in paragraphs above. In one embodiment, the personal mobile processing device is selected from the group consisting of a mobile phone, a personal laptop computer, a personal tablet computer, a personal notebook computer, a personal digital assistant and a personal music player. Other mobile processing devices which are capable of processing the signals obtained from the sensing devices may also be used. The sensing device may be coupled to the personal mobile processing device via a data communication port described above. In one embodiment, the sensing device is coupled to the personal mobile processing device in a cableless configuration, that is, without the use of wires or cables extending from the personal mobile processing device to the sensing device. In one embodiment, the sensing device is substantially smaller than the palm of an average adult.

The sensing device disclosed herein may be an optical measurement device for obtaining non-invasive physiological measurements from a portion of living tissue. The force transmitting member and/or force detector disclosed herein may be part of a pressure detection assembly configured to detect and/or display an amount of pressure applied by a body part of a user to the device during the optical measurement. When a user applies an appropriate amount of pressure to the optical measurement device, the resulting signal-to-noise ratio of the detected optical measurement signal, such as a photoplethysmography signal, can be increased, and a more accurate measurement can be obtained from the user. An optimum pressure can be determined in real-time by analyzing the detected optical measurement signal and correlating a high signal-to-noise ratio portion of the signal with a corresponding applied pressure. The user is then provided real-time feedback indicating whether the amount of pressure being applied by the user should be increased, decreased or maintained at the same level in order to continually obtain the highest quality signal. The optical measurement device can therefore provide an optimal pressure determination customized for each individual user, thereby obtaining a resulting optimal measurement signal for each user. In this regard, the sensing device may comprise or may be coupled to a feedback unit configured to correlate the quality of the detected signal with the amount of applied pressure and provide feedback related to the correlation to the user as described above.

The feedback may be an indication of whether the user should adjust the amount of pressure being applied to the illumination and detection assembly. The feedback may display a range of optimal applied pressures along with the actual applied pressure being applied by the user. The range of optimal applied pressures may correspond to a state of zero transmural pressure. The feedback may be a request to the user to increase, decrease or maintain the applied pressure. The feedback may be a real-time visual output of the detected signal and detected applied pressure. The feedback unit may be a portable computer including a processor, memory and a display.

The wave emitter and wave detector disclosed herein may be part of an illumination and detection assembly configured to output light to a portion of a living tissue of a user and detect transmitted or reflected light as a signal. The detected signal may be a photoplethysmography (PPG) signal.

The illumination and detection assembly, pressure assembly and feedback unit may be integrated into a portable device. The portable device may be configured with a plurality of illumination and detection assemblies and a plurality of pressure assemblies. The illumination and detection assembly and the pressure assembly may communicate with the feedback unit over a wireless network.

There is also provided a method for detecting a physiological signal using an optical measurement device comprising: illuminating a portion of living tissue of a user and detecting transmitted or reflected light as a signal using an illumination and detection assembly disclosed above; detecting an amount of pressure applied by the portion of living tissue of the user to the illumination and detection assembly using a pressure detection assembly disclosed above; correlating the quality of the detected signal with the amount of applied pressure; and providing feedback related to the correlation to the user using a feedback unit disclosed above The method may include providing an indication to the user of whether the amount of pressure being applied to the illumination and detection assembly should be adjusted. The method may include displaying a range of optimal applied pressures along with the actual applied pressure being applied by the user. The method may include providing a range of optimal applied pressures along which corresponds to a state of zero transmural pressure. The method may include requesting the user to increase, decrease or maintain the applied pressure. The method may include displaying a real-time visual output of the detected signal and the detected applied pressure. The method may include providing feedback on a display of a computer with a processor and a memory.

There is also provided a computer program product for detecting a physiological signal using an optical measurement device, the computer program product embodied on a computer readable medium and when executed by a computer with a processor and a memory, performs the method comprising: illuminating a portion of living tissue of a user and detecting transmitted or reflected light as a signal using an illumination and detection assembly disclosed above; detecting an amount of pressure applied by the portion of living tissue of the user to the illumination and detection assembly; correlating the quality of the detected signal with the amount of applied pressure; and providing feedback related to the correlation to the user.

Exemplary embodiments described herein also seek to provide a device and method capable of augmenting signal to noise ratio in an optical signal of an illuminated region at a measuring site of a body part of a user. Exemplary embodiments also provide for detecting the optical response formed by both light reflected from the measuring site and the light transmitted through the measuring site. Exemplary embodiments described herein utilize redirecting reflections of light on its way towards the measuring site (i.e. blood vessels) back to the region of interest.

In an additional exemplary embodiment, the device may perform a series of calibration steps for each individual user in order to determine an optimum range of pressure for each individual. The subsequent steps of capturing the PPG signal will then use the predetermined optimum range as the benchmark for obtaining an optimum PPG signal.

BRIEF DESCRIPTION OF THE DRAWINGS

Example embodiments of the invention will be better understood and readily apparent to one of ordinary skill in the art from the following written description, by way of example only, and in conjunction with the drawings, in which.

DETAILED DESCRIPTION OF DRAWINGS

Figure 1A:
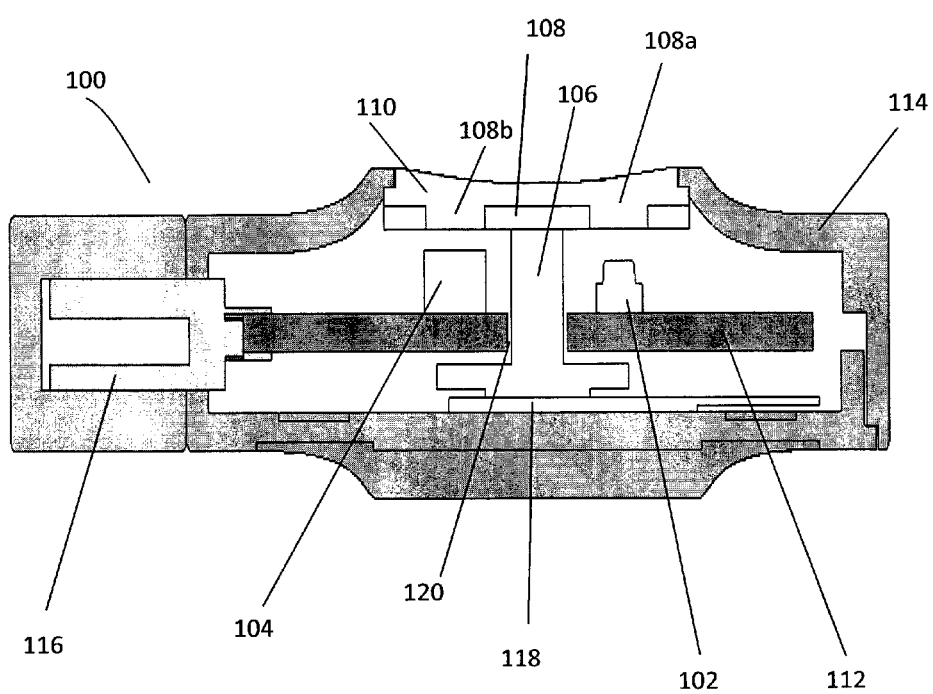
FIG. 1A is a cross-sectional view of a sensing device in accordance with one embodiment disclosed herein.

Referring to FIG. 1A, there is shown a cross-sectional view of an optical measurement sensing device 100 in accordance with one embodiment disclosed herein. The sensing device 100 comprises a wave emitter in the form of a light emitting diode 102 and a wave detector in the form of a photodetector 104 disposed on the same horizontal plane (relative to the sensing device base) and on the same substrate, which is in the form of a printed circuit board 112. The substrate or printed circuit board 112 further comprises an opening 120 disposed between the LED 102 and photodetector 104. A force transmitting member comprising a plastic assembly piece 106 and an overhead portion 108, is arranged such that the plastic assembly piece 106 extends through the opening 120, between the light emitting diode 102 and the photodetector 104. The overhead portion 108 is provided to increase the overall surface area available to substantially prevent light emitted by the LED 102 from travelling directly to the photodetector 104. In this exemplary embodiment, the overhead portion 108 is disposed on the plastic assembly piece such that both of them are at an orientation substantially perpendicular to each other, i.e. the angle formed between the longitudinal axis of the overhead portion 108 and the longitudinal axis of the plastic assembly piece 106 is about 90°. The overhead portion 108 can also be provided in other forms, shapes and/or orientation so long as it serves to substantially prevent light emitted by the LED 102 from travelling directly to the photodetector 104. The overhead portion 108 can be a detachable portion that is attached to the plastic assembly piece 106. Alternatively, the overhead portion 108 can be a continuous part of the plastic assembly piece 106 formed as a single structure. The plastic assembly piece 106 is opaque and substantially does not allow light from the light emitting diode 102 to travel directly to the photodetector 109. The overhead portion 108 is also opaque. However, the overhead portion 108 comprises access hole 108a for allowing light emitted from the light emitting diode 102 to pass through and access hole 108b for allowing reflected light to pass through to reach the photodetector 104. As can be seen in FIG. 1A, the force transmitting member 106 together with the overhead portion 108 as a whole appears to have a "T" cross-sectional shape. The positioning and the structure of the force transmitting member substantially prevent light emitted by the light emitting diode 102 from traveling directly to the photodetector 104. The force transmitting member is rested on a sensing substrate in the form of force sensor 118. The force sensor 118 can be provided as a flexible printed circuit that senses contact force and provides the associated electrical signal to the printed circuit board 112 via the electrical connectors at one end of the force sensor 118 (not shown in FIG. 1.). Due to its flexibility, the force sensor 118 is able to deform slightly when the force transmitting member transmits a force to the metal connector 118. The sensing device 100 also comprises a plastic housing 114 for housing the individual components described above. At the top of the housing 114, there is provided an orientation-free measurement surface in the form of a transparent plastic piece 110 for receiving a surface portion of the user to be detected. The orientation-free measurement surface in the form of the transparent plastic piece 110 is not limited to a single orientation at which the surface portion of the user must be placed. For example, as compared to a clip or a cuff, the orientation-free measurement surface does not require the surface portion of the user to be engaged therewith in a particular fashion, so long as the user surface in contact with the orientation-free measurement surface is capable of reflecting the emitted waves towards the wave detector. As such, the orientation-free measurement surface is capable of advantageously detecting a 2-dimensional surface. On the other hand, the portion of the user to be detected must be 3-dimensional when a clip or a cuff is used, in order to ensure sufficient engagement with the clip or the cuff for detection. The transparent plastic piece 110 may further provide an additional layer of protection, to prevent direct contact and damage to the LED and photodetector. It may also serve to prevent dust and small particles from entering the housing of the sensing device.

The sensing device 100 also comprises a coupling member in the form of a data communication port 116 electrically coupled to the printed circuit board 112. The data communication port 116 is capable of transmitting electrical signals to and from the sensing device 100. The data communication port 116 is also capable of transmitting electrical power to power the printed circuit board 112 and its electrically connected components such as the light emitting diode 102 and the photodetector 104 and force sensor 118.

In use, the sensing device 100 is connected to a personal mobile processing unit for example a mobile phone via the data communication port 116. The user then places a desired surface to be detected, for example a finger, onto the transparent plastic piece 110. Light emitted from the light emitting diode 102 travels through the access hole 108a and towards the finger surface in contact with the transparent plastic piece 110. The emitted light that is reflected from the finger surface passes through access hole 108b and towards the photodetector 104. The photodetector 104 then transmits an electrical signal representative of the detected reflected light to the mobile phone via the data communication port 116. At the same time, the exerted force is transmitted via the plastic assembly piece 106 towards the force detector 118. The force detector 118 then provides an electrical signal representative of the force with the circuit board 112. The electrical signal is then transmitted to the mobile phone via the data communication port 116. The mobile phone may comprise a processing unit to process the signals received from the sensing device 100. The mobile phone may also comprise a feedback unit to indicate to the user whether the force exerted by the finger is too high or low. The user may then adjust the force or pressure accordingly and once the optimum pressure is detected, the mobile phone will display the physiological characteristics that are derived from the properties of the reflected light detected.

Figure 1B:
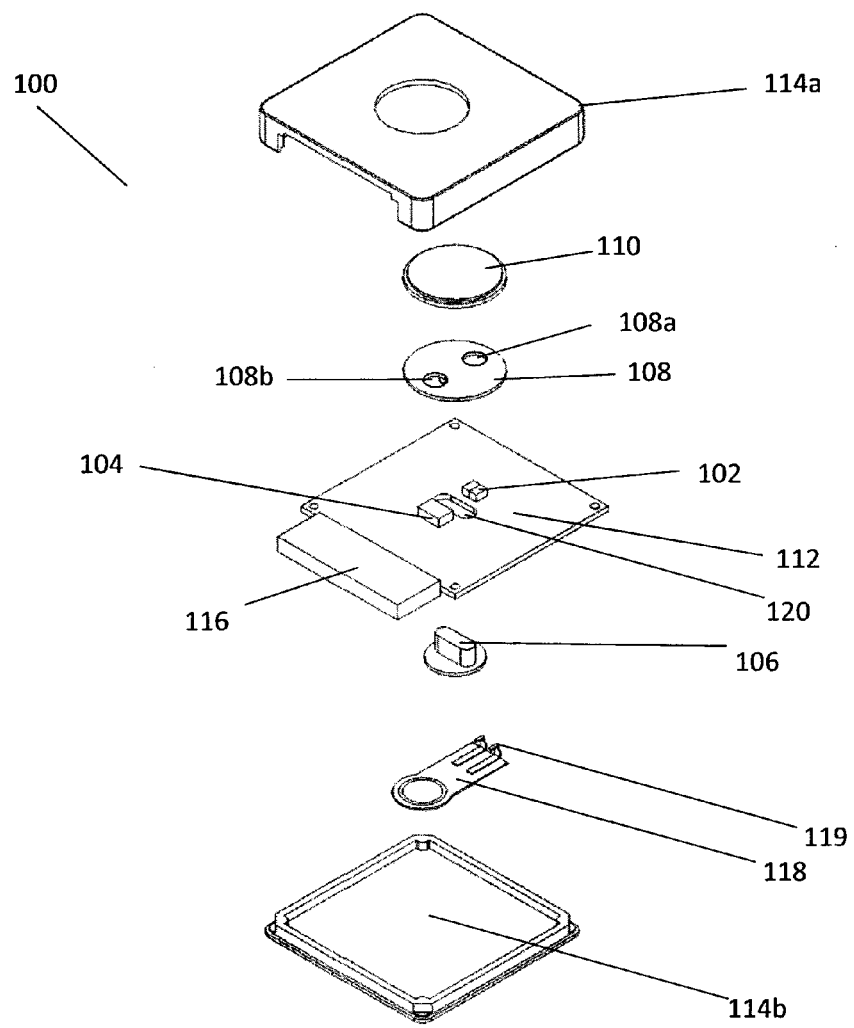
FIG. 1B is an exploded view of the sensing device of FIG. 1A.

FIG. 1B is an exploded view of the sensing device 100 of FIG. 1A. The individual components are dismantled and can be clearly seen. The plastic housing 114 can be seen to be separated into a top portion 114a and a bottom portion 114b. The force sensor 118 senses contact force and provides the associated electrical signal to the printed circuit board 112 via the electrical connectors 119 at one end of the force sensor 118

Figure 1C:
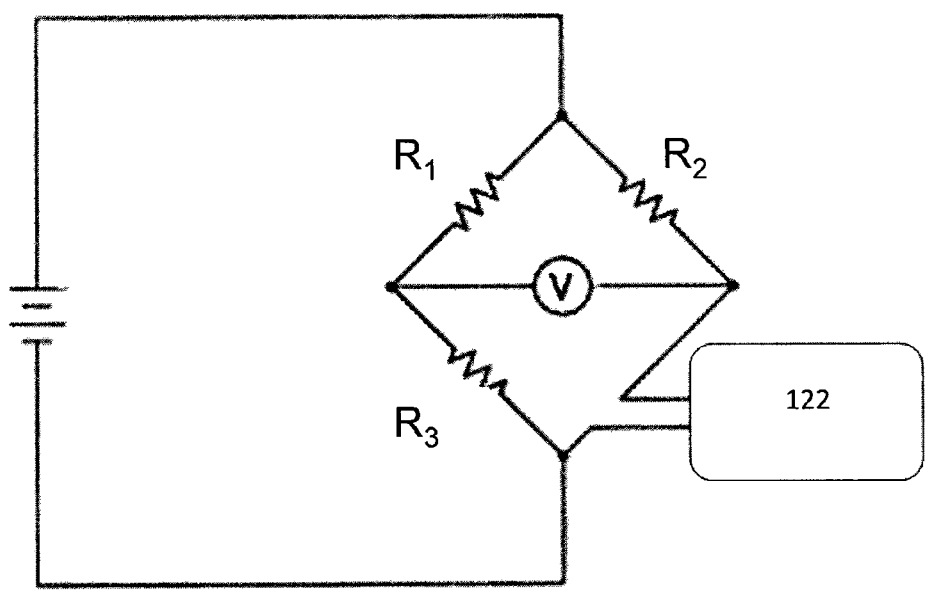
FIG. 1C is a simplified exemplary representative circuit diagram for implementing one embodiment of the piezo-based sensor disclosed herein.

FIG. 1C shows a simplified exemplary representative circuit diagram for implementing one embodiment of the piezo-based sensor disclosed herein. V represents a voltmeter. $R_1$, $R_2$ and $R_3$ represent electrical resistors. Component 122 represents a piezo-based material (e.g. piezoelectric or piezoresistive) which can be depicted as one or more electric resistors, one or more of which being variable resistors with resistance being dependent on the force applied thereto. It will be appreciated by a skilled person that the position of Component 122 can be interchanged with any one of $R_1$, $R_2$ and $R_3$ or vice versa if desired. $R_1$, $R_2$, $R_3$ and Component 122 are connected in a Wheatstone bridge configuration. The bridge configuration shown in FIG. 1C is in the quarter-bridge configuration. Nevertheless, if desired, the bridge can also be operated in the half or full form, that is, with one or more components similar to Component 122 replacing $R_2$ or all of $R_1$, $R_2$ and $R_3$ respectively. One or more fixed or variable electrical resistors can also be added as "dummy" force gauges to complete the bridge circuit as and when desired, for example to negate the effects of temperature changes.

In one example working implementation when the bridge is operated in a quarter configuration shown in FIG. 1C, $R_3$ is set to a value equal to the resistance of Component 122 with no force applied. $R_3$ can be a variable resistor to allow ease of setting to zero. The other two resistors $R_1$ and $R_2$ are set to be equal to each other. In such arrangement, when no force is applied to Component 122, the bridge becomes symmetrically balanced, that is, the voltmeter V indicates zero volts, representing zero force on component. When force is being applied to Component 122, its resistance decreases or increases, respectively, thus unbalancing the bridge and producing a non-zero reading on the voltmeter. The readings obtained on the voltmeter can then be correlated to the actual mechanical force applied on component 122.

Figure 2A:
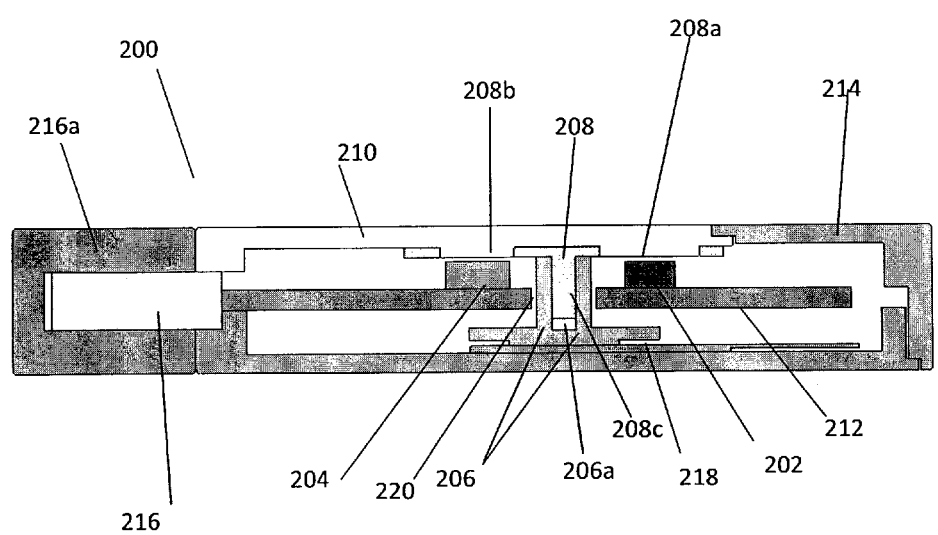
FIG. 2A is a cross-sectional view of a cantilever type sensing device in accordance with another embodiment disclosed herein.

FIG. 2A is a cross-sectional view of a cantilever type sensing device in accordance with another embodiment disclosed herein. The sensing device 200 comprises a wave emitter in the form of a light emitting diode 202 and a wave detector in the form of a photodetector 204 disposed on the same horizontal plane (relative to the sensing device base) and on the same substrate, which is in the form of a printed circuit board 212. The substrate or printed circuit board 212 further comprises an opening 220 disposed between the LED 202 and photodetector 204. A force transmitting member comprising a plastic assembly piece 206 and an overhead portion 208, is arranged such that the plastic assembly piece 206 extends through the opening 220, between the light emitting diode 202 and the photodetector 204. The overhead portion 208 is provided to increase the overall surface area available to substantially prevent light emitted by the LED 202 from travelling directly to the photodetector 204. In this exemplary embodiment, the overhead portion 208 is inserted into the plastic assembly piece such that both of them fit snuggly with each other. The overhead portion 208 can also be provided in other forms, shapes and/or orientation so long as it serves to substantially prevent light emitted by the LED 202 from travelling directly to the photodetector 204. The overhead portion 208 can be a detachable portion that is attached to the plastic assembly piece 206. Alternatively, the overhead portion 208 can be a continuous part of the plastic assembly piece 206 formed as a single structure. The plastic assembly piece 206 is opaque and substantially does not allow light from the light emitting diode 202 to travel directly to the photodetector 209. The overhead portion 208 is also opaque. However, the overhead portion 208 comprises access hole 208a for allowing light emitted from the light emitting diode 202 to pass through and access hole 208b for allowing reflected light to pass through to reach the photodetector 204. As can be seen in FIG. 2A, the force transmitting member 206 as a whole appears to have a forked shaped cross sectional area to allow the overhead portion 208 to rest thereon. The forked shaped cross sectional area provides stability to the overhead portion 208 and also facilitates transmission of an exerted force via a cantilever type moment. From the side view, the forked shape cross sectional area appears to comprise a base having a plurality of walls (for e.g. two walls) extending from the base such that the walls are substantially perpendicular to the base. From the side view, the walls are spaced at a distance from each other. From a three-dimensional perspective, the force transmitting member 206 can in fact be a circumferential wall extending from a base having the forked shaped cross sectional area described above. The circumferential wall may be continuously joined such that it forms a enclosure around a space on the base (as shown for example in component 206 of FIG. 2B). The circumferential wall can be annular shaped or in any other shape as long as it forms an enclosure around a space on the base. In other embodiments, it is also possible that the circumferential wall comprises one or more gaps to disrupt its continuity but may nevertheless still be considered to generally surround a space on the base. Due to the wall/s extending from the base, the space on the base that is surrounded by the wall/s may be deemed as a recess or cavity. In some other cases, the walls may be deemed as a built up area around the space on the base. The overhead portion 208 can have a protrusion 208c that is complementary to this recess or cavity such that the protrusion of the overhead portion 208 can be inserted into the recess or cavity 206a within the plastic assembly piece 206 to provide a more snug or rigid fit. It will be appreciated that in some exemplary embodiments this complementary mating structure may be reversed such that the recess or cavity now exists on the overhead portion and the protrusion exists on the force transmitting member.

The positioning and the structure of the force transmitting member 206 substantially prevents light emitted by the light emitting diode 202 from traveling directly to the photodetector 209. The force transmitting member is rested on a sensing substrate in the form of force sensor 218. The force sensor 218 can be provided as a flexible printed circuit that senses contact force and provides the associated electrical signal to the printed circuit board 212 via the electrical connectors at one end of the force sensor 218 (not shown in FIG. 2A.). Due to its flexibility, the force sensor 218 is able to deform slightly when the force transmitting member transmits a force to the metal connector 218. The sensing device 200 also comprises a plastic housing 214 for housing the individual components described above. At the top of the housing 214, there is provided an orientation-free measurement surface in the form of a transparent plastic piece 210 for receiving a surface portion of the user to be detected. The orientation-free measurement surface in the form of the transparent plastic piece 210 is not limited to a single orientation at which the surface portion of the user must be placed. For example, as compared to a clip or a cuff, the orientation-free measurement surface does not require the surface portion of the user to be engaged therewith in a particular fashion, so long as the user surface in contact with the orientation-free measurement surface is capable of reflecting the emitted waves towards the wave detector. As such, the orientation-free measurement surface is capable of advantageously detecting a 2-dimensional surface. On the other hand, the portion of the user to be detected must be 3-dimensional when a clip or a cuff is used, in order to ensure sufficient engagement with the clip or the cuff for detection. The transparent plastic piece 210 may further provide an additional layer of protection, to prevent direct contact and damage to the LED and photodetector. It may also serve to prevent dust and small particles from entering the housing of the sensing device.

The sensing device 200 also comprises a coupling member in the form of a data communication port 216 electrically coupled to the printed circuit board 212. The data communication port 216 is capable of transmitting electrical signals to and from the sensing device 200. The data communication port 216 is also capable of transmitting electrical power to power the printed circuit board 212 and its electrically connected components such as the light emitting diode 202 and the photodetector 204 and force sensor 218.

In use, the sensing device 200 is connected to a personal mobile processing unit for example a mobile phone via the data communication port 216. The user then places a desired surface to be detected, for example a finger, onto the transparent plastic piece 210. Light emitted from the light emitting diode 202 travels through the access hole 208a and towards the finger surface in contact with the transparent plastic piece 210. The emitted light that is reflected from the finger surface passes through access hole 208b and towards the photodetector 204. The photodetector 204 then transmits an electrical signal representative of the detected reflected light to the mobile phone via the data communication port 216. A cover 216A may be provided for the data communication port 216. At the same time, the exerted force is transmitted via the plastic assembly piece 206 towards the force detector 218. The force detector 218 then provides an electrical signal representative of the force with the circuit board 212. The electrical signal is then transmitted to the mobile phone via the data communication port 216. The mobile phone may comprise a processing unit to process the signals received from the sensing device 200. The mobile phone may also comprise a feedback unit to indicate to the user whether the force exerted by the finger is too high or low. The user may then adjust the force or pressure accordingly and once the optimum pressure is detected, the mobile phone will display the physiological characteristics that are derived from the properties of the reflected light detected.

Figure 2B:
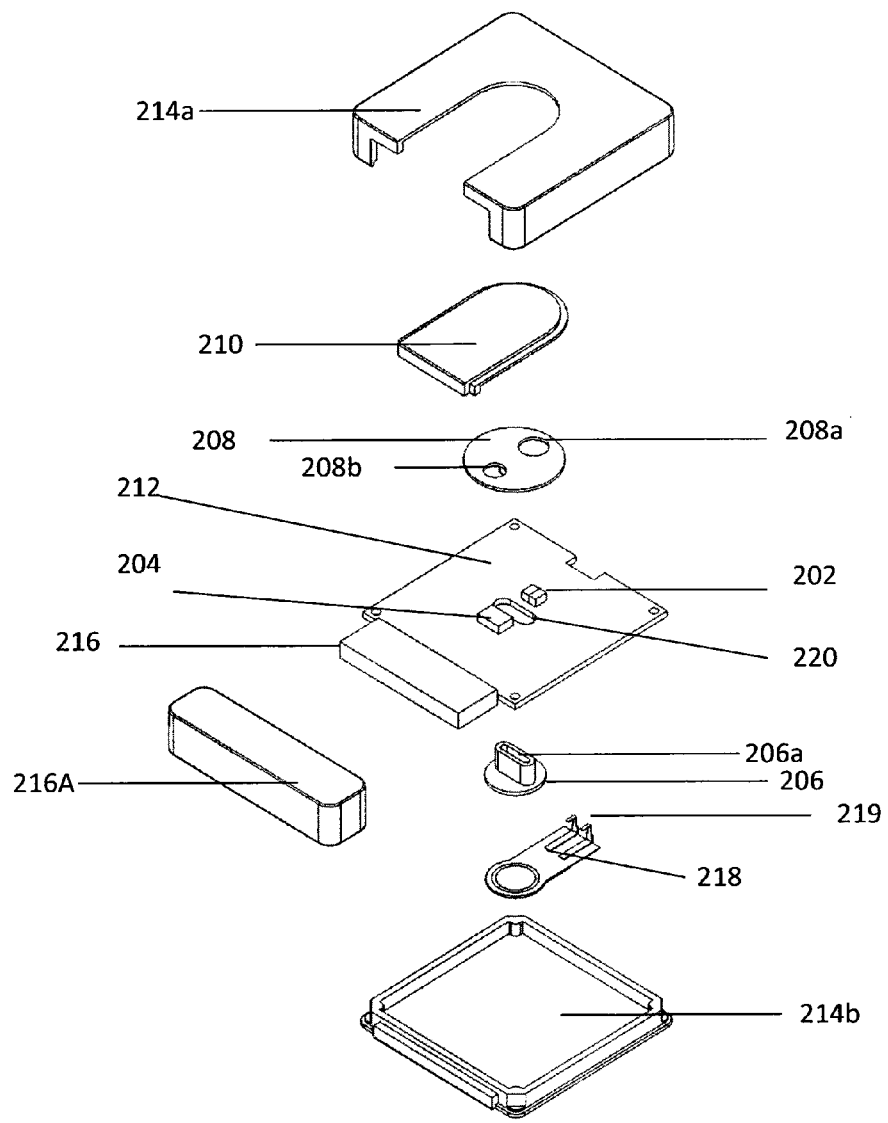
FIG. 2B is an exploded view of the sensing device of FIG. 2A.

FIG. 2B is an exploded view of the sensing device of FIG. 2A. The individual components are dismantled and can be clearly seen. The plastic housing 214 can be seen to be separated into a top portion 214a and a bottom portion 214b. The force sensor 218 senses contact force and provides the associated electrical signal to the printed circuit board 212 via the electrical connectors 219 at one end of the force sensor 218.

Figure 2C:
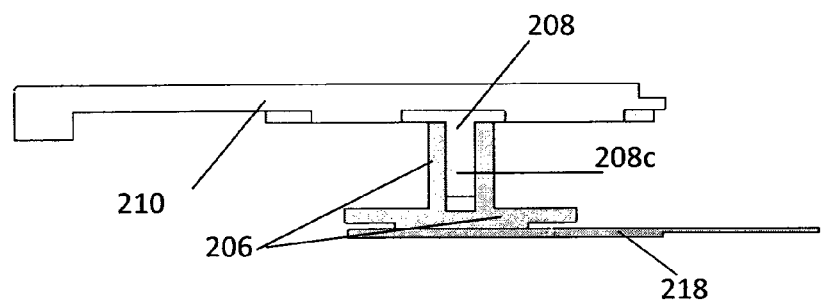
FIG. 2C is a simplified view of FIG. 2A showing only the main components that may be useful for transmittance and sensing of an exerted force.

FIG. 2C is a simplified view of FIG. 2A showing only the main components that may be useful for the transmission and the sensing of an exerted force through a cantilever type moment. The cantilever structure can restrict movement of the column in all direction except one. This can give the column better stability and easy for user to maintain a constant applied force.

Figure 2D:
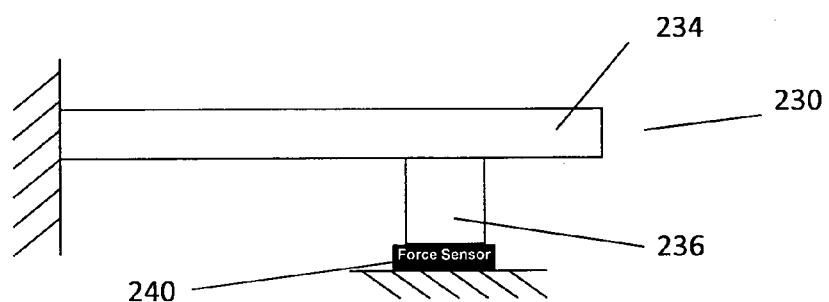
FIG. 2D and FIG. 2E are schematics of an exemplary cantilever type force application.
Figure 2E:
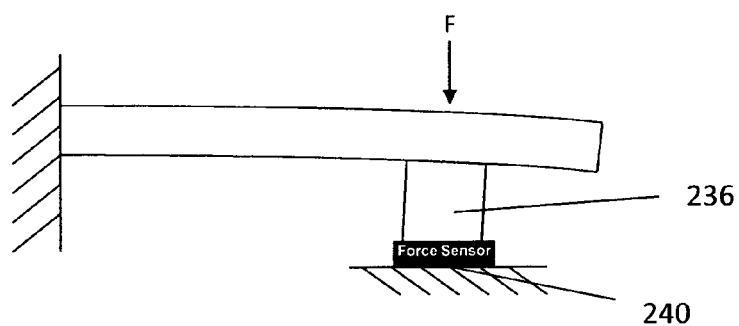

FIG. 2D and FIG. 2E show schematics of an exemplary cantilever type force application 230. Component 234 can be taken to be a simplified representation of the transparent plastic piece 210 together with the overhead portion 208 of FIG. 2B, Component 236 can be taken to be a simplified representation of the force transmitting member 206 of FIG. 2B, and Component 240 can be taken to be a simplified representation of the force detector 218 of FIG. 2B. When force F is applied on Component 234 towards Component 236, a bending moment occurs resulting in deformation of Component 234 and Component 236 towards one direction. This bending moment is transmitted to Component 240 for detection.

Figure 2F:
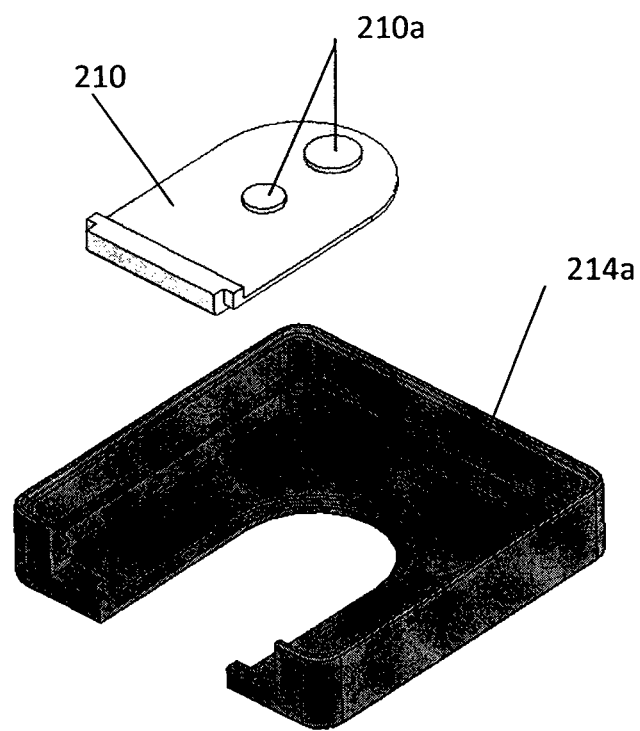
FIG. 2F is a perspective view of the underside of the transparent plastic piece and the top portion of the plastic housing of FIG. 2B.

FIG. 2F is a perspective view of the underside of the transparent plastic piece 210 and the top portion of the plastic housing 214a of FIG. 2B. As shown in FIG. 2F, the transparent plastic piece 210 comprises protrusions 210a that are able to fit into the access holes 208a and 208b of the overhead portion 208 of FIG. 2B in order to secure and prevent undesirable lateral movement of the transparent plastic piece 210.

Figure 2G:
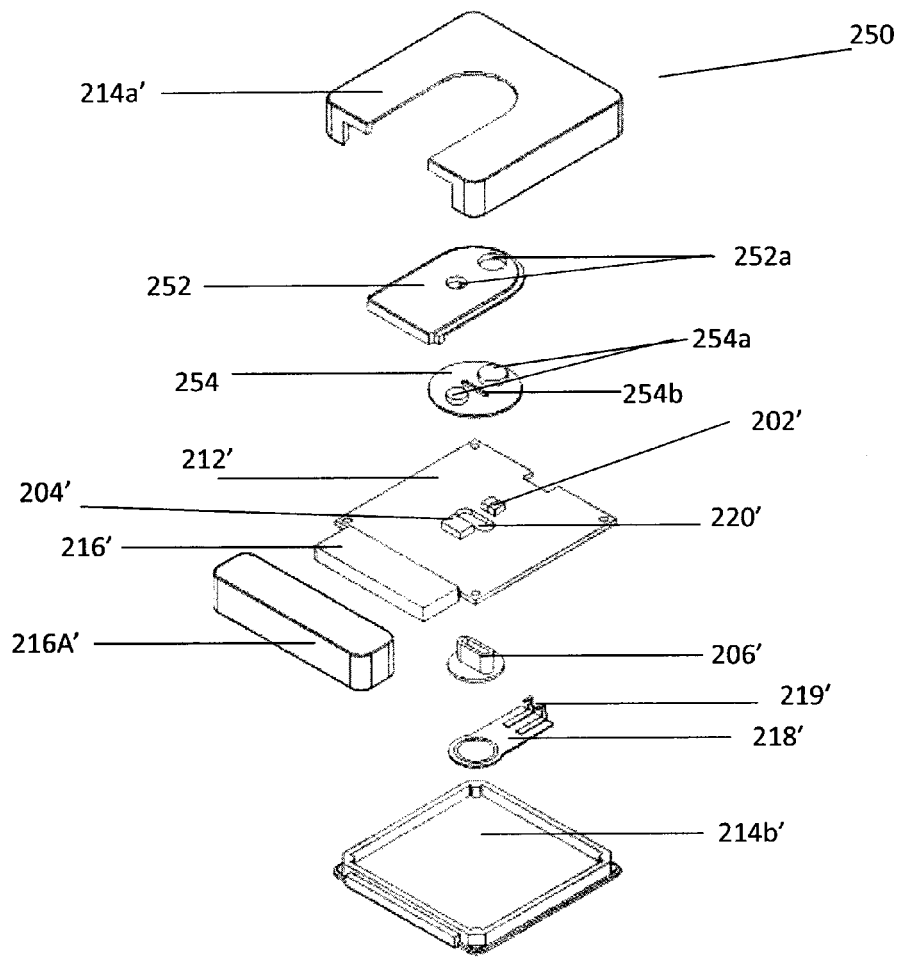
FIG. 2G is an exploded view of another exemplary embodiment of the sensing device disclosed herein.

FIG. 2G is an exploded view of another exemplary embodiment of the sensing device 250 disclosed herein. In this exemplary embodiment, most of the components are similar to those described in FIG. 2B. These similar elements are labelled with the same reference numerals used in FIG. 2B but with the inclusion of the prime symbol '. In this exemplary embodiment, the main differences from the embodiment of FIG. 2B are the components 252 and 254. Component 252 is a plastic piece that is opaque or substantially opaque (allows minimal light to pass through) but has access holes 252a to allow light to pass through. Component 254 is an overhead portion similar to the overhead portion 208 of FIG. 2B. However, component 254 is substantially transparent which can allow light to pass through. Further, protrusions 254a (which are also transparent), are present instead of the access holes 208a and 208b shown in FIG. 2B. The protrusion 254a are able to fit into the access holes 252a of the opaque or substantially opaque plastic piece 252 in order to secure and prevent undesirable lateral movement of the plastic piece 252. It will be appreciated that this configuration is reversed from that shown in FIG. 2F.

Figure 2H:
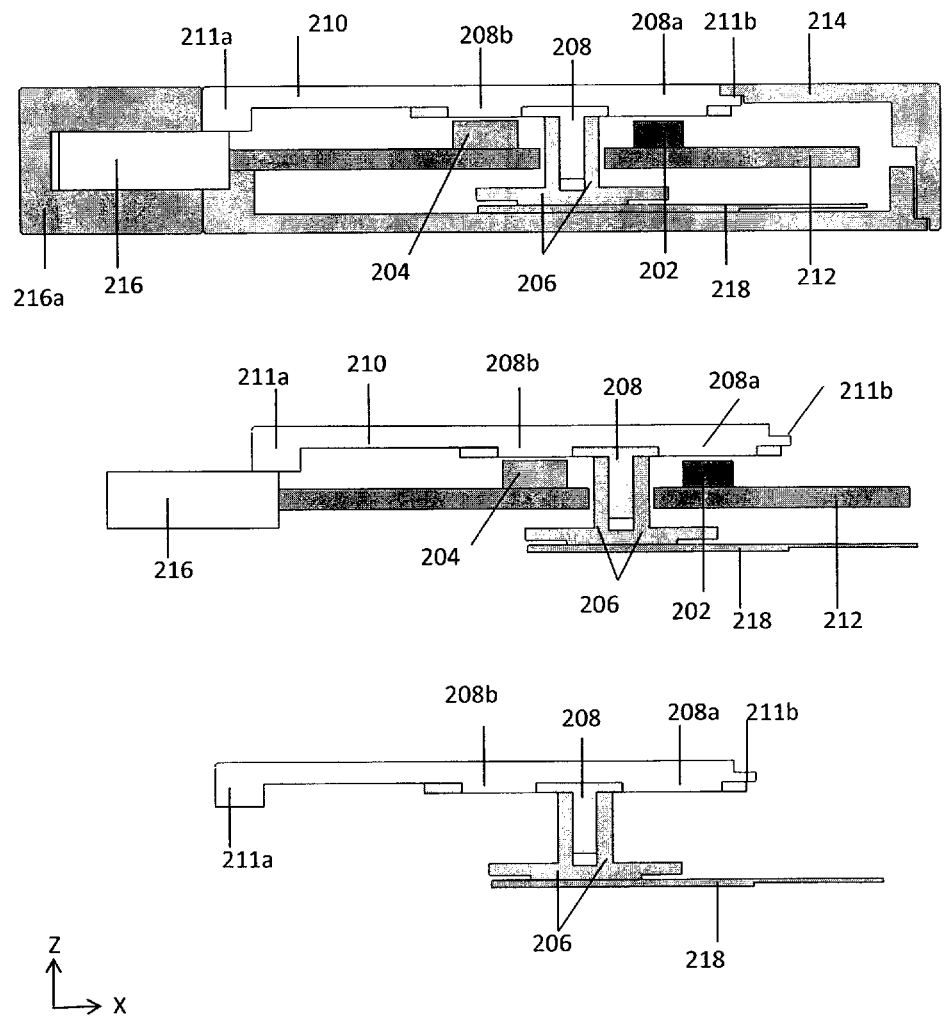
FIG. 2H is a cross-sectional view of an assembled sensing device of FIG. 2A at various levels of stripping to emphasize the structure of the transparent plastic piece.

FIG. 2H is a cross-sectional view of an assembled sensing device of FIG. 2A at various levels of stripping to emphasize the structure of the transparent plastic piece. As shown in FIG. 2H, the transparent piece 210 has a fulcrum end 211a that fits snugly into the casing 214, such that lateral movements in the plane defined by the X and Y coordinate axes (the Y axis being the axis going into the page and the X axis being the axis going from the left to the right of the page from the viewer's perspective) are restricted. The opposite end 211b is free to move downwards along the Z coordinate axis (the Z axis being the axis going from bottom to top of the page from the viewer's perspective). However, the transparent piece 210 has a stepped outer edge such that the bottom surface is wider than its top surface. The casing 214 is correspondingly dimensioned to only fit the smaller top surface, but not the bottom surface. Therefore, because the larger bottom surface is restricted from moving out of the casing surface, upward movement of the cantilever transparent piece cannot exceed the default position. When attempts are made to move the cantilever transparent piece 210 upwards, the stepped edge at the opposite end 211b engages with a complementary stepped edge of casing 214, thus arresting upward movement from its predetermined position. This can prevent the transparent piece 210 from falling out of the casing 214 and can also allow the measurement of an accurate default pressure, where no external force is applied. In certain embodiments a resilient means such as a spring can be coupled to the stepped edge at the opposite end 211b to return it to its original configuration when a user exerted downward force on it is removed. The resilient means can also urge the stepped edge at the opposite end 211b towards the casing 214 for engagement thereto, when the user exerted force on opposite end is removed. When fully assembled, the fulcrum end 211a of the transparent plastic piece 210 (acting as a cantilever) can sit on top of the communication port 216, as shown in FIG. 2H. In certain embodiments a resilient means such as a spring can be present between the transparent plastic piece 210 and the communication port 216. It can be seen in FIG. 2H that the transparent plastic piece 210 is perched at the end of the communication port 216 such that part of 211a is free and not in contact with the communication port 216. This can possibly allow some clockwise rotation (from the viewer's perspective of FIG. 2H) of the plastic piece 210 when a force is applied at the opposite end. As the transparent plastic piece 210 can also act as a cantilever, the transparent plastic piece 210 can be substantially flexible but at the same time have sufficient flexural strength to withstand the force exerted by the user during a PPG measurement. The transparent plastic piece 210 may also have sufficient flexural strength and/or elasticity to return it back to its original shape/position when the exerted force is removed. In some other exemplary embodiments, the transparent plastic piece 210 may be coupled to a resilient means such as a spring which returns the transparent plastic piece 210 back to its original configuration once the exerted force is removed. With complementary mating structures present among the different components, it will be appreciated that the exemplary sensing device can be easily assembled to form a rigid and stable assembly which arrests undesired movement. This can allow the sensing device to have a high level of measurement accuracy and consistency by reducing the number of unknown or variable parameters present (for e.g. caused by undesired movement of the components). Another advantage of the complementary mating structures would be that the individual components can be reversibly assembled or disassembled from each other, making repairs or replacement of the individual components convenient. It will also be appreciated that the exemplary sensing device with its individual complementary mating structures can be adapted into a snap-fit design for easier assembly and disassembly.

Figure 2I:
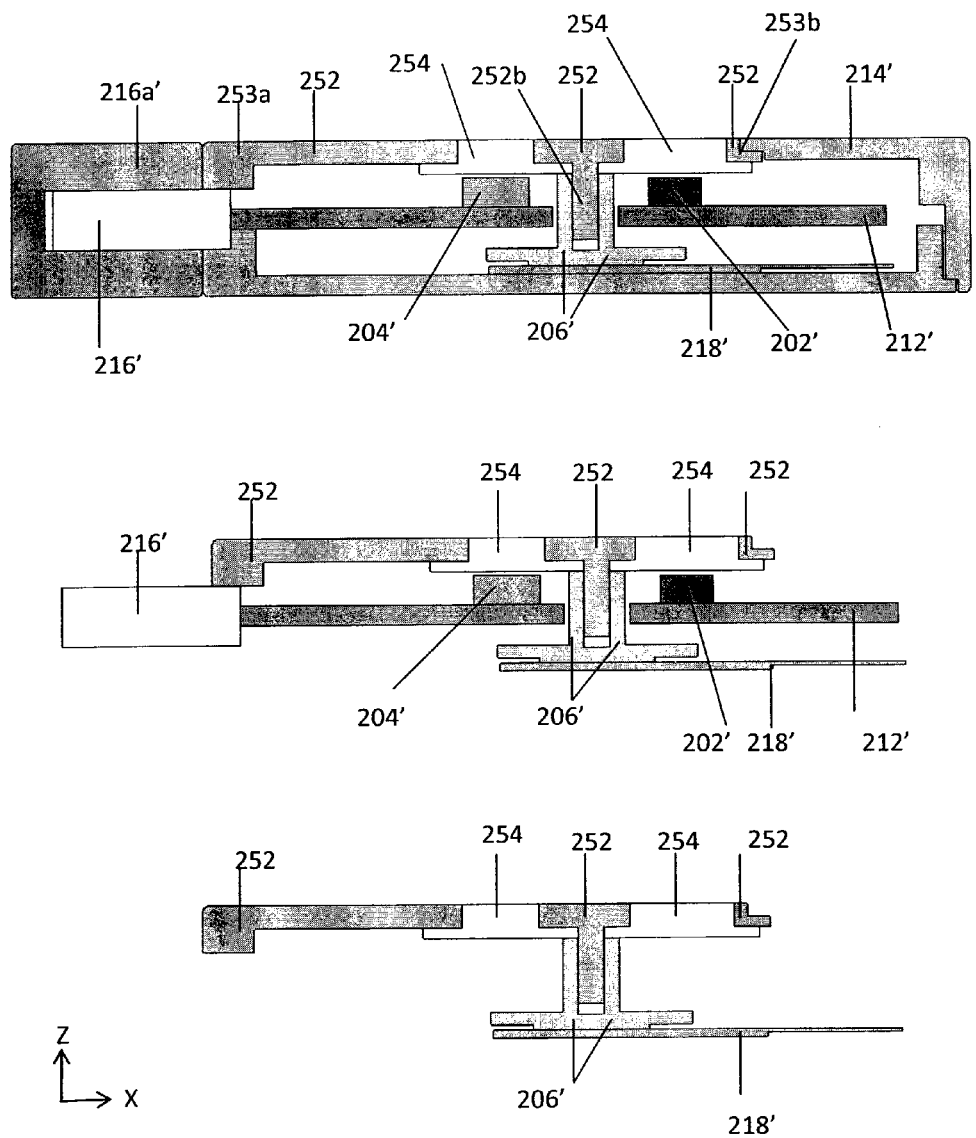
FIG. 2I is a cross-sectional view of an assembled sensing device of FIG. 2G, at various levels of stripping to emphasize the structure of the opaque or substantially opaque plastic piece.
Figure 3:
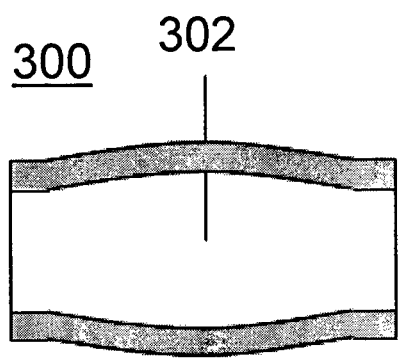
FIG. 3 is an illustration of a cross-section of a blood vessel when a low external pressure is applied.

FIG. 2I is a cross-sectional view of an assembled sensing device of FIG. 2G, at various levels of stripping to emphasize the structure of the opaque or substantially opaque plastic piece. As shown in FIG. 2I, the plastic piece 252 has a fulcrum end 253a that fits snugly into the casing 214', such that lateral movements in the plane defined by the X and Y coordinate axes (the Y axis being the axis going into the page and the X axis being the axis going from the left to the right of the page from the viewer's perspective) are restricted. The opposite end 253b is free to move downwards along the Z coordinate axis (the Z axis being the axis going from bottom to top of the page from the viewer's perspective). However, the plastic piece 252 has a stepped outer edge such that the bottom surface is wider than its top surface. The casing 214' is correspondingly dimensioned to only fit the smaller top surface, but not the bottom surface. Therefore, because the larger bottom surface is restricted from moving out of the casing surface, upward movement of the cantilever piece cannot exceed the default position. When attempts are made to move the cantilever plastic piece 252 upwards, the stepped edge at the opposite end 253b engages with a complementary stepped edge of casing 214', thus arresting upward movement from its predetermined position. This can prevent the plastic piece 252 from falling out of the casing 214' and can also allow the measurement of an accurate default pressure, where no external force is applied by the user. In certain embodiments a resilient means such as a spring can be coupled to the stepped edge at the opposite end 253b to return it to its original configuration when a user exerted downward force on it is removed. The resilient means can also urge the opposite end 253b towards the casing 214' for engagement thereto, when the user exerted force on the opposite end 253b is removed. The cantilever piece 252 comprises a further center protrusion 252b which can extend through an opening 254b (See FIG. 2G) of the overhead transparent piece 254 and be inserted into a complementary recess or cavity within the plastic assembly piece 206' to provide a more snug or rigid fit. When fully assembled, the fulcrum end 253a of the plastic piece 254 (acting as a cantilever) can sit on top of the communication port 216', as shown in FIG. 2I. In certain embodiments a resilient means such as a spring can be present between the plastic piece 252 and the communication port 216'. It can be seen in FIG. 2I that the transparent plastic piece 252 is perched at the end of the communication port 216' such that part of 253a is free and not in contact with the communication port 216'. This can possibly allow some clockwise rotation (from the viewer's perspective of FIG. 2I) of the plastic piece 252 when a force is applied at the opposite end. As the plastic piece 252 can also act as a cantilever, the plastic piece 252 can be substantially flexible but at the same time have sufficient flexural strength to withstand the force exerted by the user during a PPG measurement. The plastic piece 252 may also have sufficient flexural strength and/or elasticity to return it back to its original shape/position when the exerted force is removed. In some other exemplary embodiments, the plastic piece 252 may be coupled to a resilient means such as a spring which returns the plastic piece 252 back to its original configuration once the exerted force is removed. With complementary mating structures present among the different components, it will be appreciated that the exemplary sensing device can be easily assembled to form a rigid and stable assembly which arrests undesired movement. This can allow the sensing device to have a high level of measurement accuracy and consistency by reducing the number of unknown or variable parameters present (for e.g. caused by undesired movement of the components). Another advantage of the complementary mating structures would be that the individual components can be reversibly assembled or disassembled from each other, making repairs or replacement of the individual components convenient. It will also be appreciated that the exemplary sensing device with its individual complementary mating structures can be adapted into a snap-fit design for easier assembly and disassembly.

While in the above description, the measurement surface (which can be a transparent plastic piece or an opaque plastic piece), the overhead portion and the force transmitting member appear to be described as separate components, they may in some embodiments be taken to be parts of a single overall functional component that achieves the cantilever moment when a force is exerted. Therefore, in some embodiments, the plastic piece, the overhead portion and the force transmitting member may collectively form a single unitary structure, which as a whole, may be considered to a cantilever structure.

In addition, while it has been described above that the wave emitter may comprise a LED, in some embodiments, a wave emitter may comprise a plurality of LEDs at least one being a red LED and one being an infra-red LED.

FIG. 3 to FIG. 20 provide further exemplary illustrations, methods and/or implementations that are believed to be helpful in the understanding of the general principles of the sensing device disclosed herein.

It is preferable that in certain embodiments, the sensing device is capable of detecting/sensing a physiological signal. The acquisition of a physiological signal representing a change in the volume of an organ in the body through the use of optical measurement is known as a photoplethysmograph (PPG). Obtaining optical PPG signals typically requires application of external pressure on the body surface which is being measured. The pressure is required in order to obtain a good quality PPG signal with a high signal to noise ratio.

However, the externally-applied pressure cannot be too large or too small, or the quality of the detected PPG signal will be low. For example, as illustrated in a cross section of a blood vessel 300 in FIG. 3, in the event of an insufficient exertion of external force as compared to internal arterial pressure at a measurement site 302, the internal pressure is too low to obtain a proper measurement, and low PPG signals are obtained.

Figure 4:
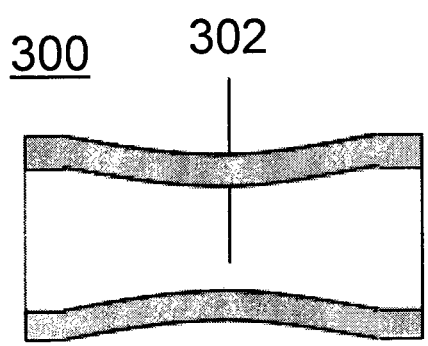
FIG. 4 is an illustration of the cross-section of the blood vessel when a high external pressure is applied.

On the contrary, as illustrated in FIG. 4, the application of too much external force causes the blood vessel 300 to be occluded at the measurement site 302 where the pressure is applied, resulting in resistance of regular blood flow and generating skewed PPG signal data. If the external pressure is too small or too high, the reaction pressure at the wall of the blood vessel 300 is low, and thus a small PPG signal will be observed.

Figure 5:
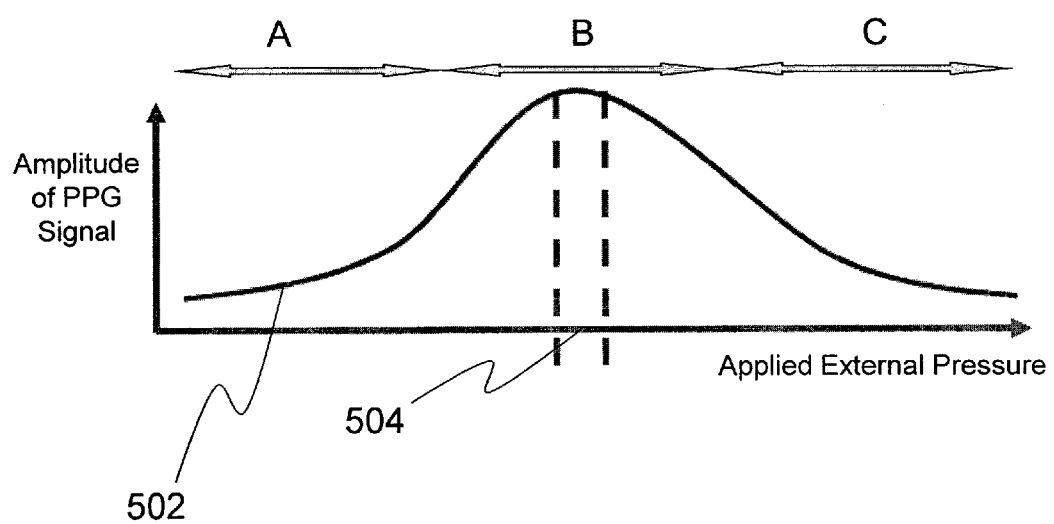
FIG. 5 is a graphical illustration of an amplitude of a PPG signal received during increasing amounts of external pressure in a state of zero transmural pressure.

FIG. 5 is a graphical illustration of the amplitude 502 of a measured PPG signal in comparison with an amount of applied external pressure. With a low applied pressure in range A, the amplitude 502 is correspondingly low. As the applied pressure is increased, in range B, the amplitude also increases. However, when the applied pressure increases beyond a certain point, the amplitude decreases again, as shown in range C. To obtain a strong PPG signal, the external pressure should be sufficient to minimize transmural pressure such that the external pressure is equal to the internal pressure. Further illustrated in FIG. 5 is a range 504 within range B where the amplitude of the PPG signal is at its peak. Within this range 504, an externally-applied pressure is instantaneously balanced with the internal arterial pressure, thus resulting in a state of zero transmural pressure. At zero transmural pressure, the arterial walls are unloaded and the arteries will not change in size. Consequently, the blood volume within the arteries at the measured region will not change and can be accurately measured to provide a good quality PPG signal.

Accordingly, to achieve the above, the force transmitting member and/or force detector disclosed herein may be part of a pressure assembly that seeks to achieve and to maintain an optimal pressure for obtaining an optimum PPG signal over an extended period of time. By providing real-time, instantaneous feedback to a user being measured, the user is able to instantly adjust the amount of pressure being applied to the device in order to obtain an optimum PPG signal. However, the optimum pressure may not only be a result of a state of zero transmural pressure, but may also result from the effects of absorption and scattering paths of light as light travels in and out of a portion of tissue of a user being measured. For example, where the pressure is too low, a light source may not be able to penetrate the tissue surrounding the blood vessel which is being measured. Therefore, light may not travel in and out of the finger effectively enough for a good PPG signal to be detected. Where the pressure is too high, light may be absorbed or scattered such that the amount of light detected is insufficient to obtain a good PPG signal.

It will also be understood that the sensing device disclosed herein may also comprise or may be coupled to feedback unit that is capable of providing feedback to the user indicating whether the user is applying insufficient pressure, too much pressure or the correct amount of pressure. The feedback to the user may be visual or auditory in the form of a visual display or audible sounds, and may particularly be a display of the real-time PPG signal being captured by the device. The feedback may also be a more simplified display indicating whether the user should take action to increase or reduce the amount of pressure being applied to the device. In another embodiment, the feedback may be in the form of tactile feedback, wherein the device produces e.g. a small vibration when the applied pressure is at an optimum range.

Figure 7:
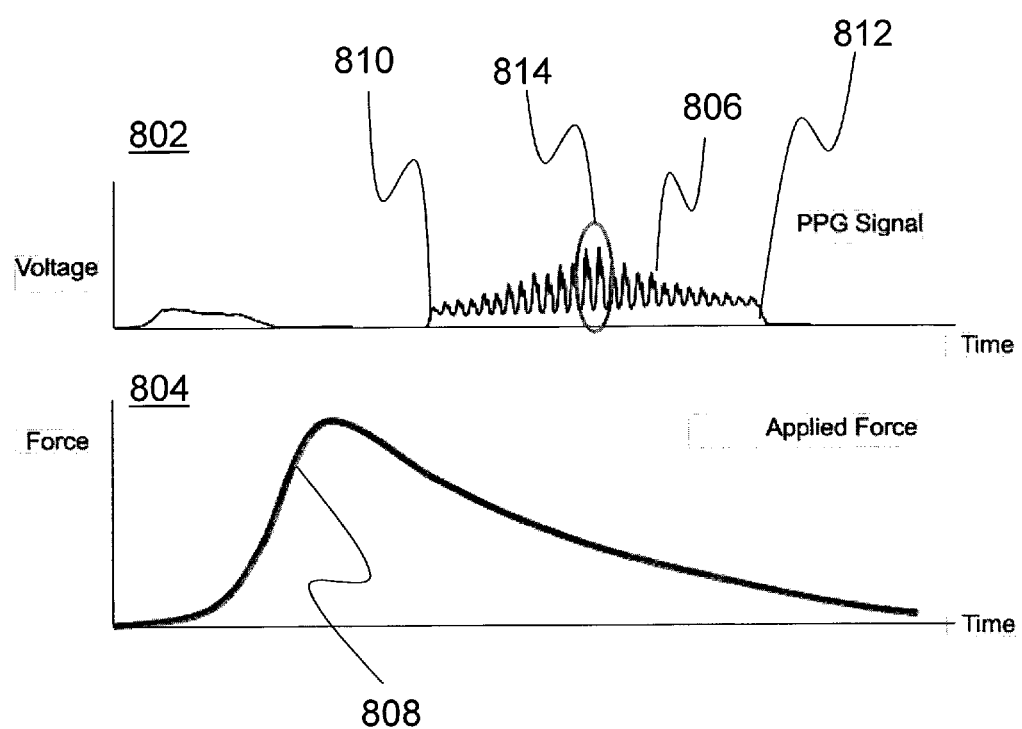
FIG. 7 illustrates a graphical comparison of a graph of measured voltage of a PPG signal over time as it corresponds to a graph of an applied amount of pressure over time.
Figures 8A, 8B:
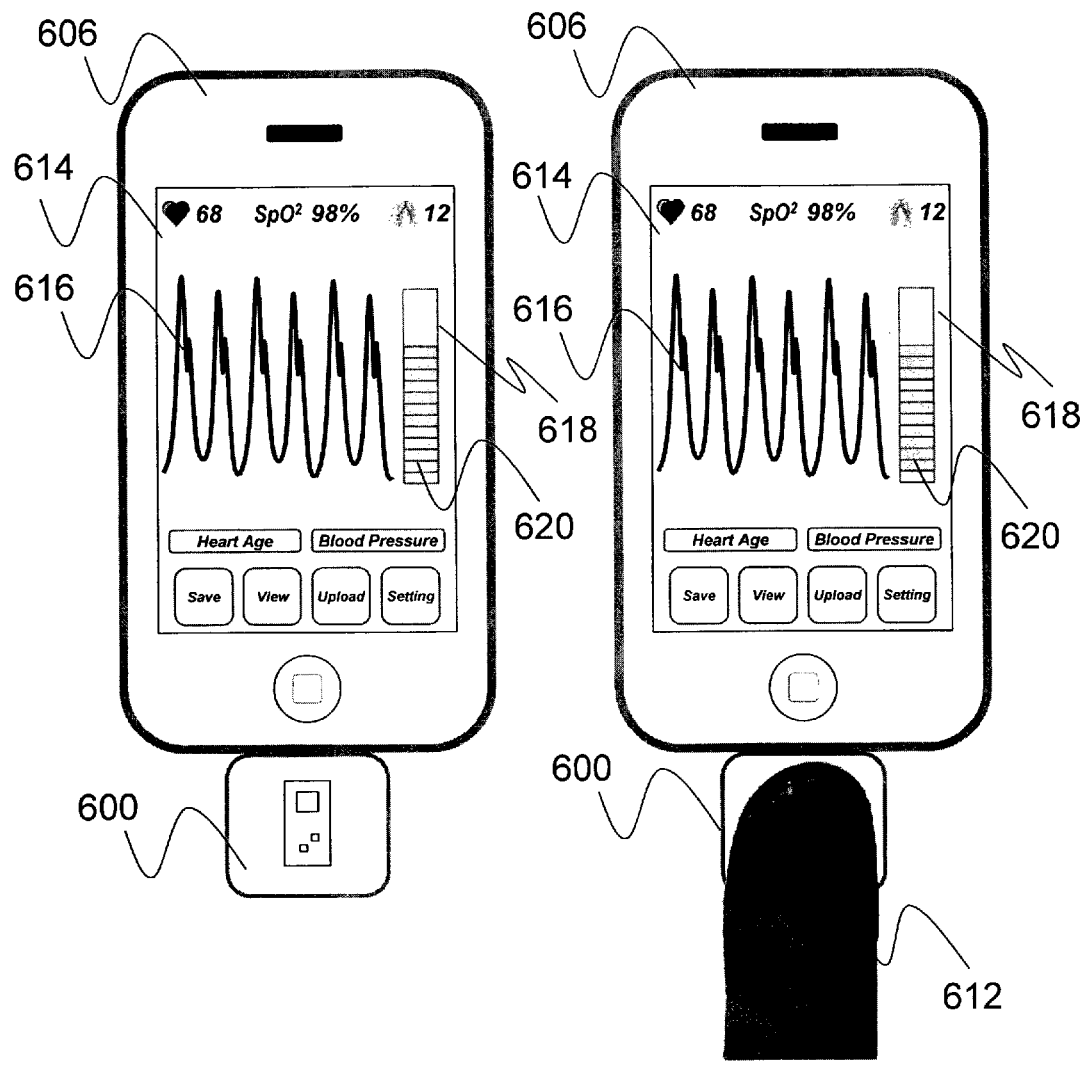
FIGS. 8A and 8B illustrate a feedback unit, such as a portable device with a display, in connection with one embodiment of the sensing device and a user's interaction therewith, according to an exemplary embodiment.
Figure 9:
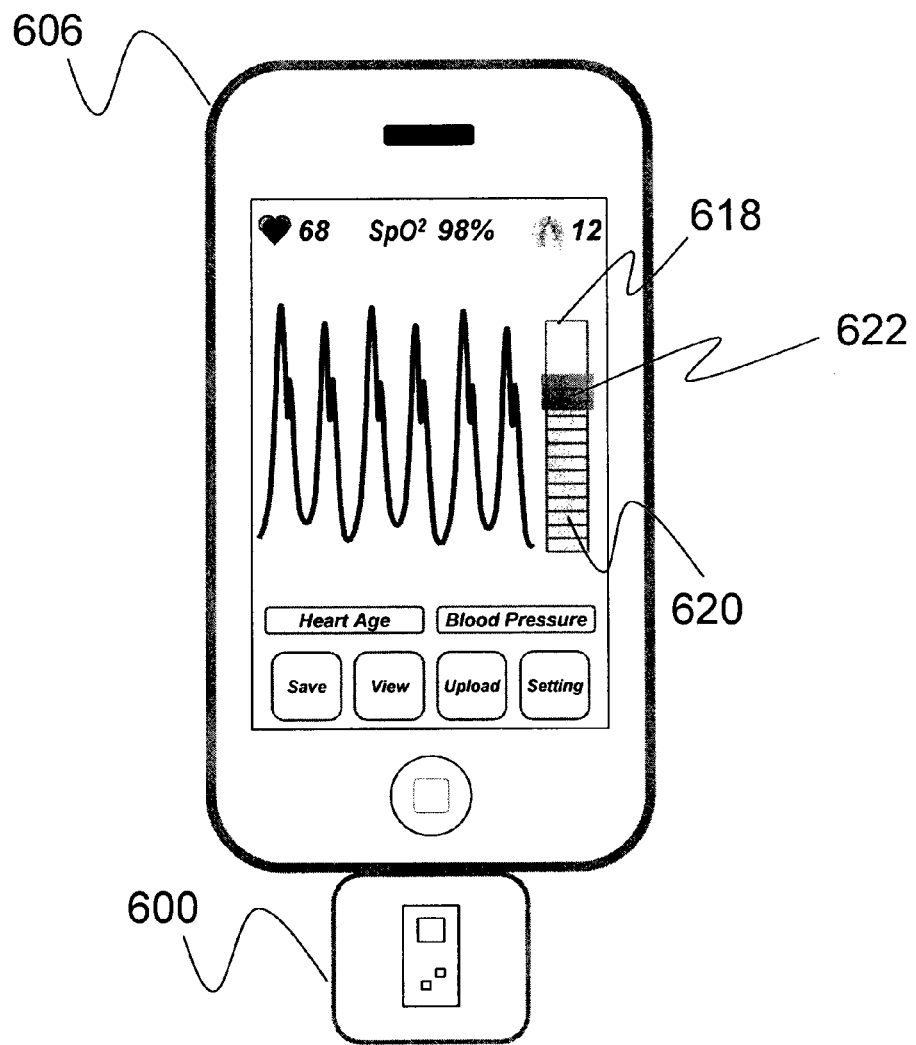
FIG. 9 illustrates a graphical user interface (GUI) on the display, including a graphical representation of a PPG signal and a graphical representation of applied pressure, according to an exemplary embodiment.

FIG. 8A illustrates one exemplary embodiment of an sensing device 600 being coupled to a feedback unit 606. The feedback unit 606 may be a computer including a processor, a memory and optionally a display, as is further described below with regard to FIG. 20. The feedback unit 606 receives a PPG signal and pressure measurements from the sensing device 600, and temporally correlates the PPG signal with the pressure measurements in order to determine an optimal amount of pressure that provides an optimal PPG signal, as shown in the comparison PPG signal graph 802 and applied pressure graph 804, illustrated in FIG. 7 and described in more detail below.

The feedback unit 606 may be provided with a display 614, as illustrated in FIGS. 8A and 8B. The display 614 may provide visual feedback to the user in the form of a graphical user interface (GUI) during the process of measuring the PPG signal. The visual feedback may be a real-time display of the detected PPG signal 616 so that the user can instantly see the effect of varying the amount of pressure being applied to the sensing device and adjust the amount of pressure until an optimum PPG signal is displayed. The display 614 may also provide a real-time graphical indication 618 of the pressure being applied. The graphical display 618 of the applied pressure may track the PPG signal 616 on the same graphical display (see FIG. 19A, below), or perhaps be displayed in the form of a vertical pressure status bar 620 positioned on one side of the displayed PPG signal, as illustrated in FIGS. 8A and 8B. The status bar 620 will move up and down depending on the amount of force being applied by the user. In this embodiment, the user identifies an optimal PPG signal in order to determine whether the displayed real-time PPG signal 616 can be improved. However, by displaying the detected PPG signal 616 and possibly the pressure status bar 620, the feedback unit 606 is not required to compute an amount of pressure that provides an optimum PPG signal, as the user is performing this step manually by analyzing the displayed PPG signal 616 and making adjustments without guidance by the device. FIG. 8B illustrates the feedback unit 606 and the sensing device 600 in operation, where a user's finger 612 is positioned on the sensing device 600.

Figure 10:
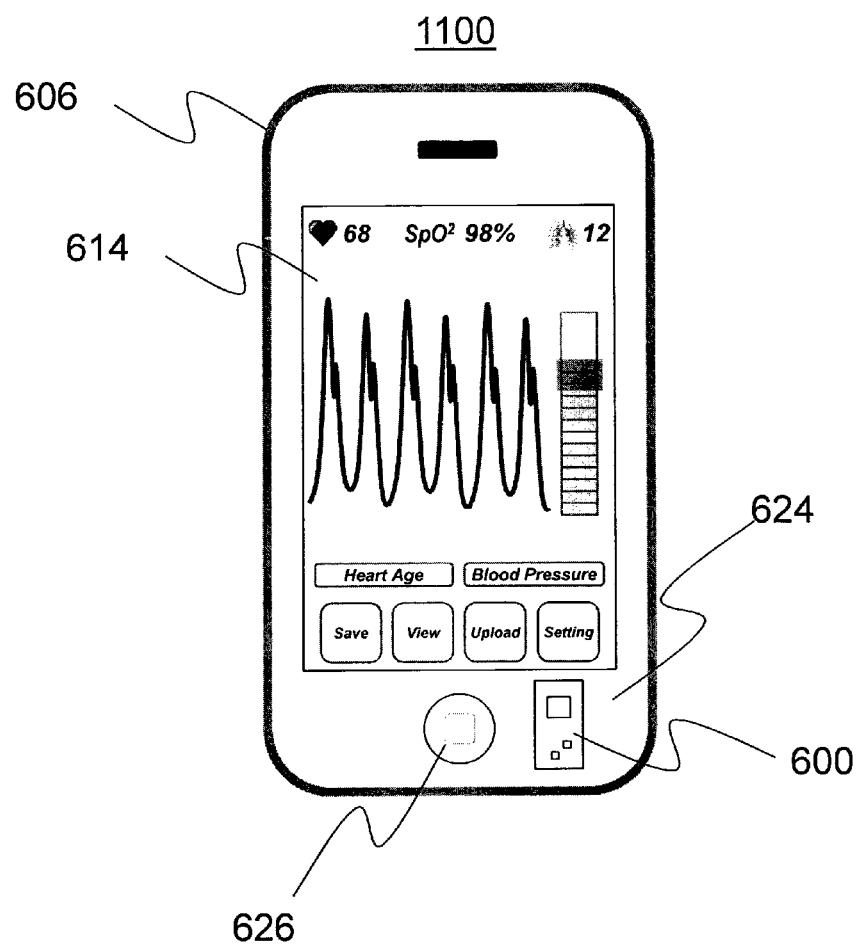
FIG. 10 illustrates a portable device integrated with a sensing device, according to an exemplary embodiment.

In an exemplary embodiment illustrated in FIG. 10, the feedback unit 606 may generate and display a GUI with a more simplified indication of whether the user should adjust the amount of pressure to provide more, less or the same amount. There may be any number of ways to provide this type of GUI. For example, symbols or shapes—perhaps even color-coded in a traffic-light colored display—may be displayed to tell the user to adjust the amount of force being applied. Similarly, the GUI may simply display words telling the user to "Apply More Pressure, "Apply Less Pressure," or "Apply the Same Amount of Pressure." In FIG. 9, a highlighted box 622 may be placed over the pressure status bar 620 to identify an optimum range at which pressure should be applied for a particular user. In this embodiment, the feedback unit 606 analyzes and compares the measured PPG signal and corresponding applied pressures in real-time in order to determine a range of applied pressure which provides the highest amplitude of PPG signal—usually a state of zero transmural pressure. The feedback unit 606 will then provide corresponding indicators to the user on the display 614 depending on whether the user is applying pressure within, above or below the determined range.

In an exemplary embodiment, the feedback unit 606 may not require a display, as it could provide audible commands to the user through a speaker or other audio output component. For example, the audio device could simply talk to the user to say "Apply More Pressure," "Apply Less Pressure," or "Apply the Same Amount of Pressure." The audio feedback could also be in the form of musical tones of different pitches or sounds—such as a ringing sound or buzzer sound—which are widely known as positive or negative sounds.

In another exemplary embodiment, the sensing device 600 may ask the user to calibrate the device before actual measurement of the PPG signal is carried out. This may involve asking the user to apply a variety of different pressures to the device during a fixed period of time, during which the feedback unit measures the PPG signal detected during that time period and determines a range of applied pressure which obtains an optimal PPG signal. For example, the user may be asked to exert pressure while following a profile of pressure ranges over a period of time, such as the force profile 808 in the applied pressure graph 804 in FIG. 7. As a result of the calibration, the device 600 is able to obtain a range of applied pressure for each individual user, rather than a generalized range which will not be accurate depending on the individual user being measured.

In one exemplary embodiment, the feedback unit 606 may be a portable device, such as a mobile phone, smartphone, personal digital assistant (PDA), tablet, netbook or laptop, although this list is not exhaustive by any means. However, the feedback unit 606 may not need to be portable, and could similarly be a computer or server. The feedback unit 606 may be connected with the optical detection device 600 in a wired or wireless fashion, or through a proprietary connector, such a universal serial bus (USB) port or the 30 pin connection used in the Apple® iPhone® (Apple Computer, Inc., Cupertino, Calif.).

Figure 15:
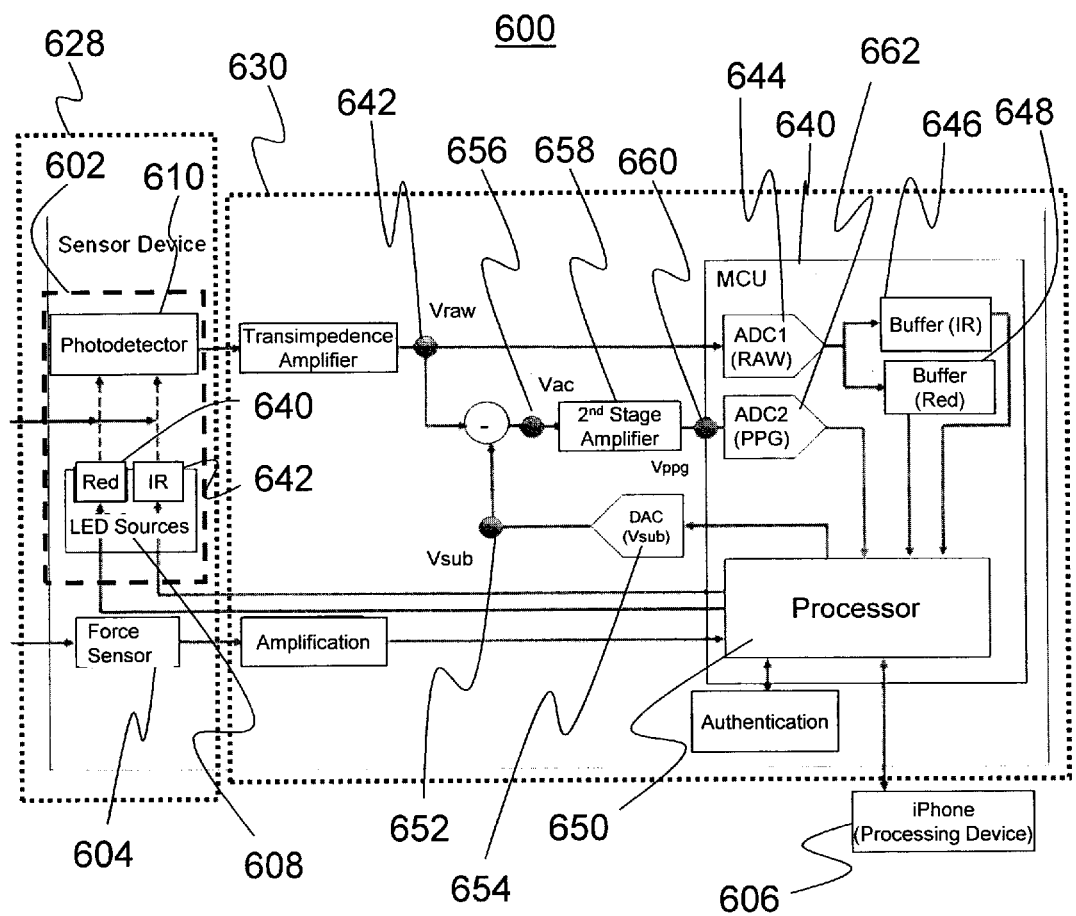
FIG. 15 is a block diagram of a sensing device, according to an exemplary embodiment.

In another embodiment, the portable device may be integrated with the sensing device as a single sensing device 1100, as shown in FIG. 10. The sensing device 600 is incorporated within a housing 624 of a portable device 606; in this case located near a menu button 626 of the portable device 606 and separate from a display 614. The illumination and detection assembly (comprising the wave emitter and detector) and the force transmitting member can be integrated with the portable device 606, thereby eliminating the need for a separate pressure detection assembly or a separate illumination and detection assembly. With such a configuration, the portable device 606 is capable of carrying out processing functions for the sensing device 600, such as signal conditioning and signal processing. As described below with regard to the block diagram in FIG. 15, the sensing device 600 integrated with the portable device 606 would only require a sensing portion 628, while a processing portion 630 would be provided by hardware and firmware of the of the portable device 606. The sensing portion 628 would include the illumination and detection assembly 602 (comprising the wave emitter and detector) and the pressure detection assembly 604, as illustrated in FIG. 15.

In another exemplary embodiment, the illumination and detection assembly may comprise a camera and flash of a smartphone or other portable device, such that the camera functions as the photodetector while the flash functions as the light source. The flash and camera would be located proximate to each other on the portable device, and the flash would be configured with a red LED and infrared LED to output the required wavelengths of light. In this exemplary embodiment, the pressure detection assembly would be the only significant modification required on the portable device.

Figure 11A:
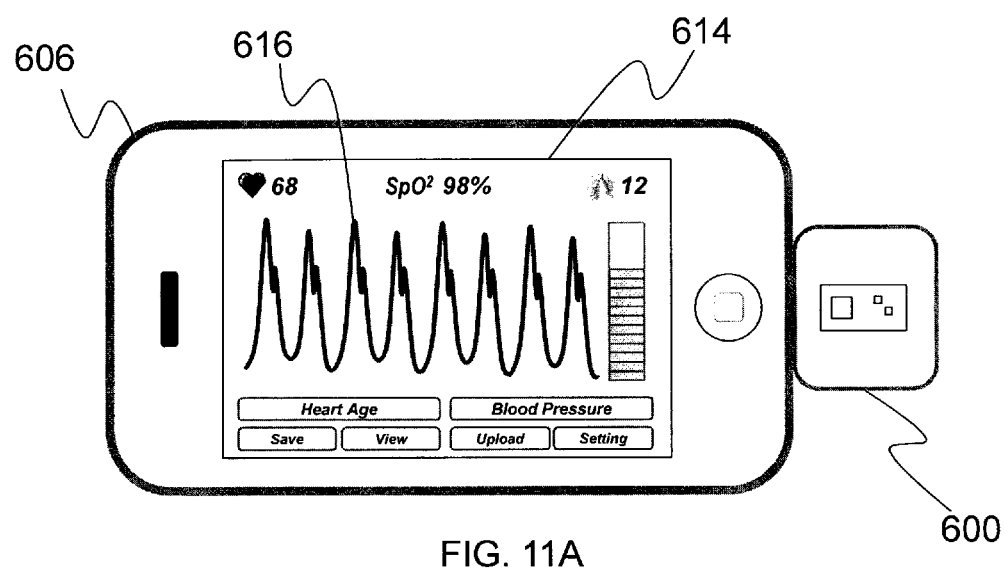
FIGS. 11A and 11B illustrate a portable device connected with a sensing device configured in a landscape orientation and a user's interaction therewith, according to an exemplary embodiment.
Figure 11B:
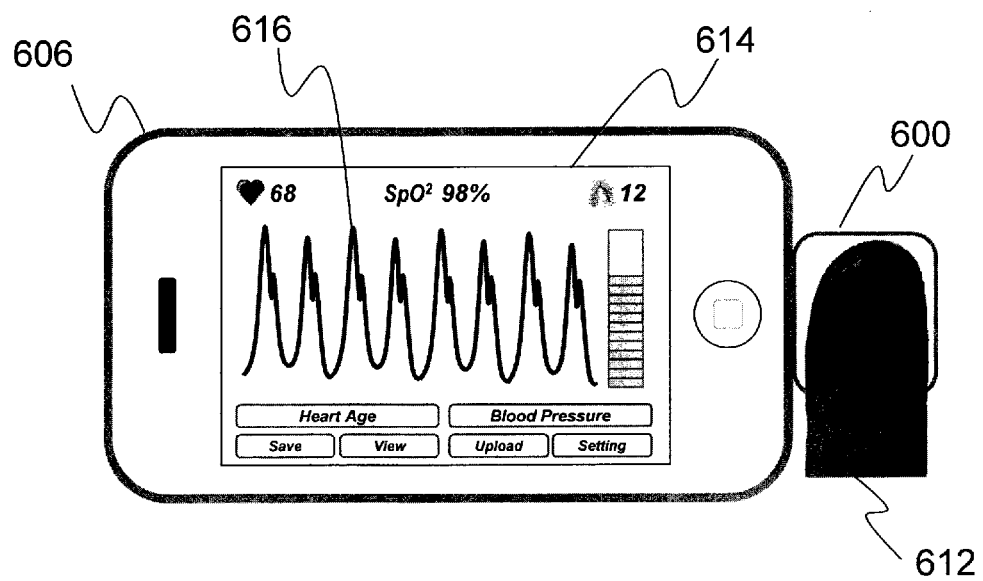

FIGS. 11A and 11B illustrate yet another exemplary embodiment, where the portable device 606 may be oriented in a landscape configuration such that the user views the display 614 horizontally and interacts with the sensing device 600 in a way that is easier for the user to hold the portable device 606 in the user's hands. In landscape orientation, the user can place a finger 612 on the sensing device 600 and more easily view a larger time period of the PPG signal 616.

Figure 12A:
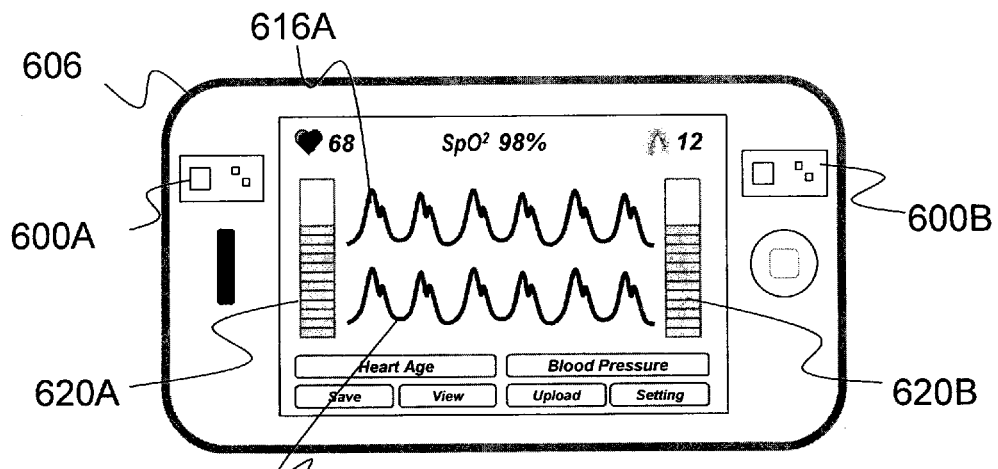
FIGS. 12A and 12B illustrate a portable device integrated with a plurality of sensing devices in a landscape orientation and a user's interaction therewith, according to an exemplary embodiment.
Figure 12B:
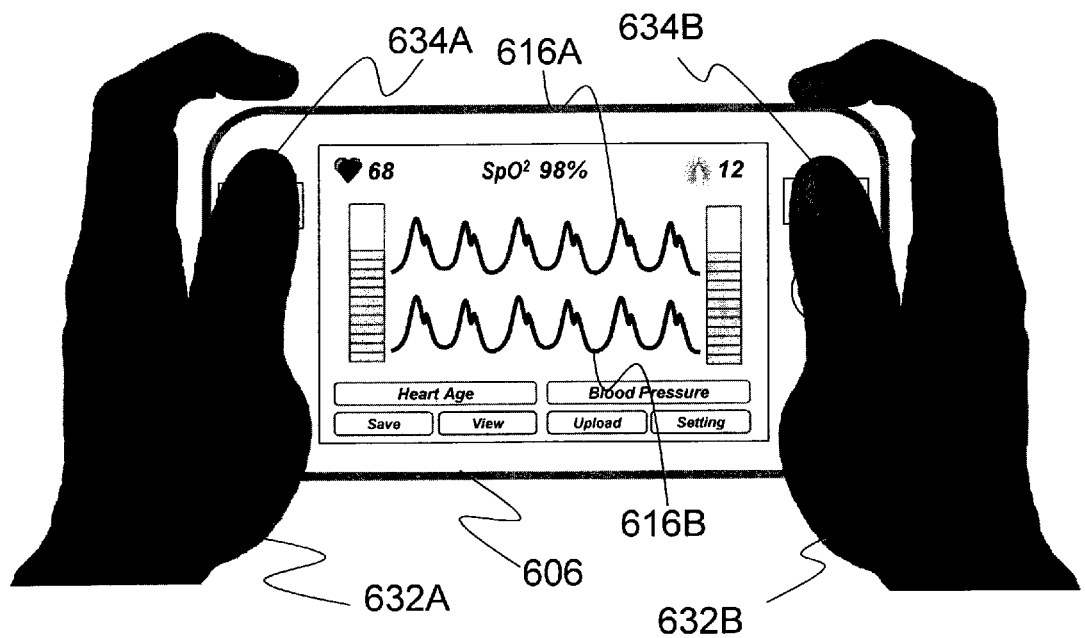
Figures 13A, 13B:
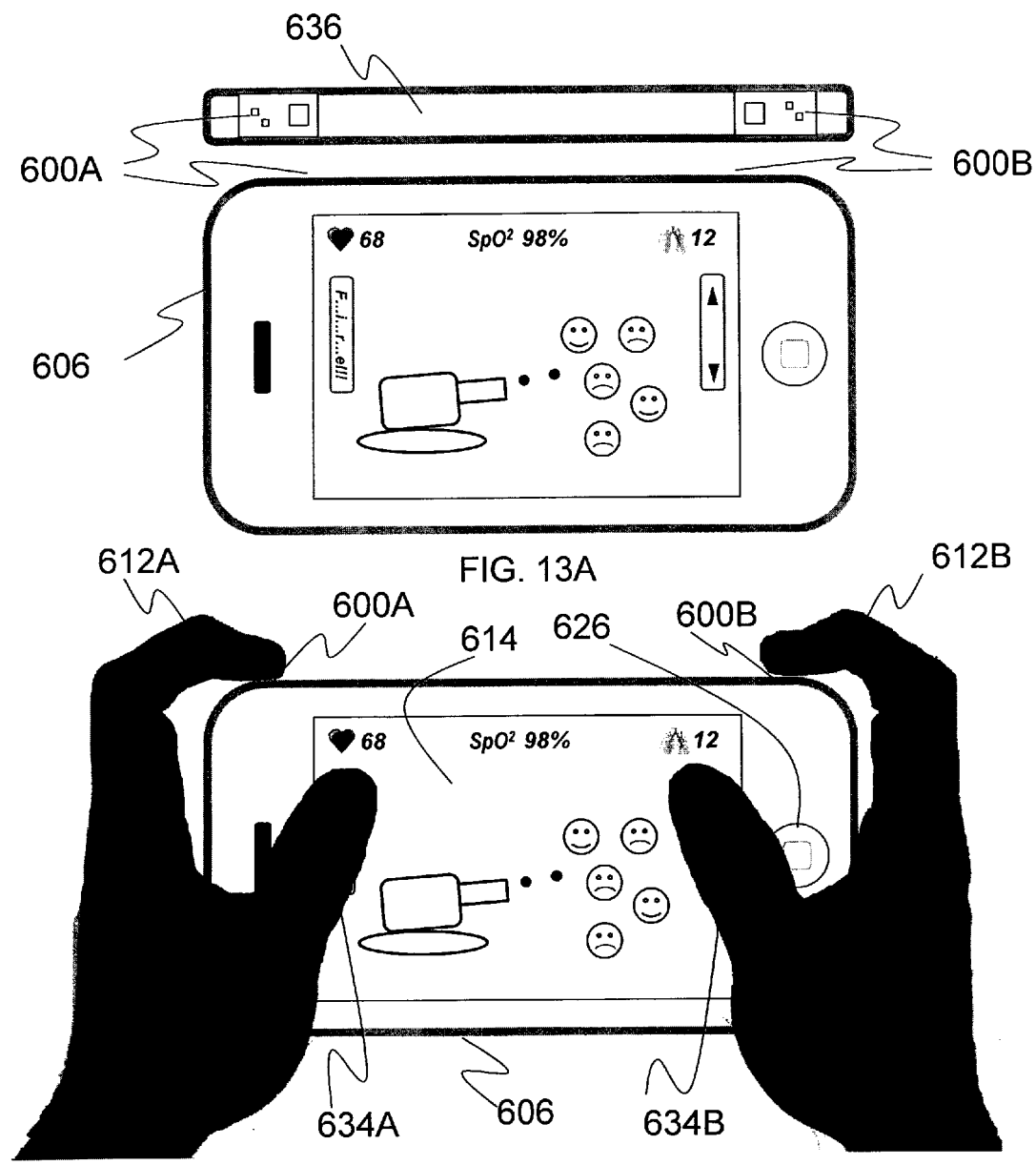
FIGS. 13A and 13B illustrate a portable device integrated with a plurality of sensing devices located on a side portion of the portable device, according to an exemplary embodiment.

FIGS. 12A and 12B illustrate another exemplary embodiment, where a plurality of sensing devices 600A and 600B are integrated with the portable device 606 for interaction with the user in a landscape orientation. The use of more than one sensing device will allow measurement of additional physiological properties, As shown in FIG. 13B, the user can easily hold the portable device 606 with both hands 632A and 632B while also placing their thumbs 634A and 634B on the corresponding sensing devices 600A and 600B. In a similar exemplary embodiment illustrated in FIGS. 13A and 13B, the sensing devices 600A and 600B may be located on a side portion 636 of the portable device 606, so that the user can place index fingers 612A and 612B in contact with the corresponding sensing devices 600A and 600B in a natural configuration. In this embodiment, the user's thumbs 634A and 634B are then free to operate the portable device by interacting with the touch screen display 614 or menu button 626 while the index fingers are being sensed by the sensing devices 600A and 600B. In the embodiments illustrated in FIGS. 12 and 13, because there are a plurality of sensing devices 600A and 600B, there may also be a corresponding plurality of PPG signals 616A and 616B and pressure status bars 620A and 620B accordingly.

The feedback unit may also include software or other computer programmable instructions which carry out instructions relating to receiving and processing the PPG signal, the pressure measurements, and creation of the output to the user relating to the correlation of the detected PPG signal and pressure measurements.

The monitoring of (i) the PPG signal from the illumination and detection assembly and (ii) the amount of force exerted by an individual from the pressure assembly thus enables the sensing device to obtain an optimum PPG signal with a high signal to noise ratio. The signal to noise ratio is augmented in an optical signal. The sensing device provides for a PPG signal to be acquired at a zero transmural pressure that is unique to each user using the device.

The resulting optimal PPG signal provides a highly accurate measurement of various physiological parameters detected by photoplethysmography, such as a saturation level of oxygen in blood.

Figure 6:
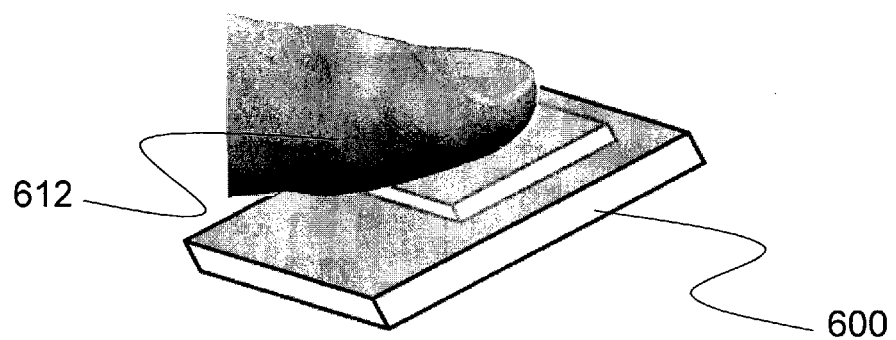
FIG. 6 is an expanded view illustration of one embodiment of a method of using the sensing device with the human finger to detect the blood pressure of the human, according to one exemplary embodiment.
Figure 14:
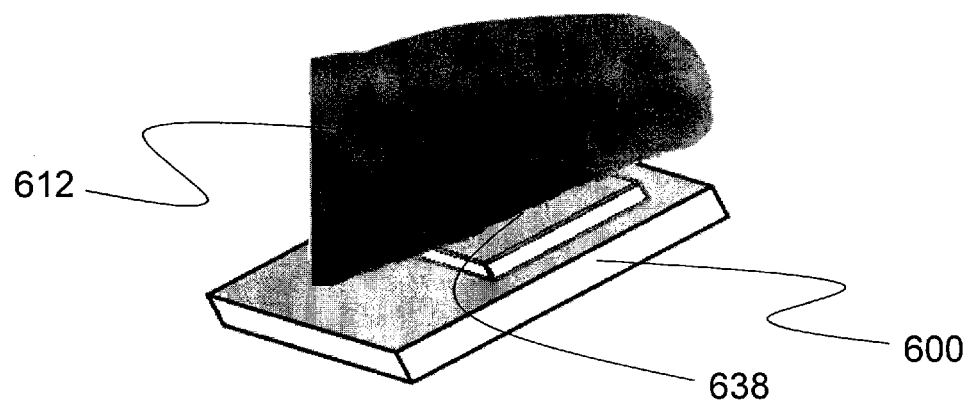
FIG. 14 is an expanded view illustration of an alternate embodiment of a method of using the sensing device with the human finger to detect the blood pressure of the human, according to one exemplary embodiment.

In another embodiment, the sensing device further includes acquisition of systolic and diastolic blood pressure parameters. One option for detecting the parameters to determine blood pressure involves placing the finger 612 face down onto the illumination and detection assembly 602 (comprising the wave emitter and detector), as illustrated in FIG. 6. Another option for detecting the parameters to determine blood pressure involves placing the side 638 of the finger 612 where the digital artery lies onto the illumination and detection assembly 602 (comprising the wave emitter and detector), as illustrated in FIG. 14. As shown in FIG. 7, a PPG signal 806 in the PPG signal graph 802 is monitored while the user applies vertical downward force onto the pressure sensor 604 following a predetermined applied force profile 808 with respect to time, as shown in the applied pressure graph 804. The basic fundamental behind this analysis is to identify when the PPG signal 806 begins to display a PPG waveform (point 810) and when the PPG signal finally dies off (point 812), as these points are indirectly associated with the highest and lowest point of the blood pressure. In addition, with this analysis, the external pressure needed to achieve zero transmural pressure can be determined. When zero transmural pressure is achieved, the PPG waveform reflects the highest amplitude, as shown at area 814 in the PPG signal graph 802. In FIG. 8, as the amount of applied pressure follows the profile 808 of rapid increase and gradual decrease over time, the PPG waveform 806 changes in amplitude accordingly. Thus, looking at the entire range of PPG waveform from 810 to 812 with respect to applied force 808, the highest amplitude PPG waveform 814 provides an indication of the corresponding position on the applied pressure graph 804 where an amount of applied pressure results in zero transmural pressure state.

One exemplary embodiment of the sensing device is described in further detail below, including its components and their relationships. In the exemplary embodiment below, the feedback unit and corresponding interface, processing and display is described for an Apple® iPhone®, although one of skill in the art will recognize that other portable devices may be used.

The illumination and detection assembly 602 (comprising the wave emitter and detector) may be connected with the feedback unit 606, in this case a portable device such as an iPhone®, using the 30 pin connector at the base of the feedback unit 606. After establishing physical connection of the illumination and detection assembly 602 with the feedback unit 606 or any other form of processing device, a microcontroller unit (MCU) 640 (see FIG. 16) in the illumination and detection assembly 602 extracts information for authentication purposes prior to sending of data to the feedback unit 606 or any other form of processing device. This authentication process may be specific to the iPhone®, as Apple® requires that any device using the 30 pin connector purchase an authentication token from Apple®.

With the example of an iPhone®, communication is enabled via the Universal Asynchronous Receiver/Transmitter (UART) protocol from the 30 pin connector of the iPhone®. Strings of data are sent to UART every 8 milliseconds from the MCU of the illumination and detection assembly 602 to the iPhone®.

The data is comprised of 2 bytes of header and 10 bytes of payload. The payload is sub-divided into 5 parts, each comprising 2 bytes of data: DC1(IR), DC2(Red), PPG1 (IR), PPG2 (Red) and FS (Force Sensor). This data is obtained in a HEX file format and is then converted to back to voltage (V).

DC1 and DC2 provide information for the DC component of the PPG waveform, thus enabling calculation for saturation of peripheral oxygen, or SpO2. PPG1 and PPG2 establish the actual PPG waveform and provide information for the AC component of the PPG waveform. FS sets out to provide information of the amount of pressure applied to the illumination and detection assembly 602. An example of the data decoding format is show in Table 1, below.

A raw PPG signal includes DC and AC components, both of which containing information critical for waveform analysis. Signal conditioning is therefore performed in order to obtain the information for further processing at the feedback unit. One embodiment of the signal conditioning process will be described below, and may be carried out by components of the illumination and detection assembly 602 illustrated in the block diagram of FIG. 16.

To determine the DC component of the PPG signal, the raw signal 642 obtained from a photodetector 610 is digitized at ADC1 644. The digitized signal will be passed on to both buffer (IR) 646 and buffer (Red) 648 accordingly, which will store up to 100 samples each before sending collated data to the processor 650.

Using the raw samples, a baseline DC component can be determined by the processor 650. At the processor 650, the digital values for Vsub (IR) and Vsub (RED) (i.e. the DC components) are calculated. The Vsub signals 652 are subsequently converted by a digital-to-analog converter (DAC) 654.

The determined DC component (Vsub) is then subtracted from the raw signal, Vraw to obtain Vac 656. The new raw signal, Vac 656, then undergoes a second stage amplification at a second stage amplifier 658 to obtain Vppg 660, where the signal to noise ratio is improved compared with Vraw 642.

Figure 16A:
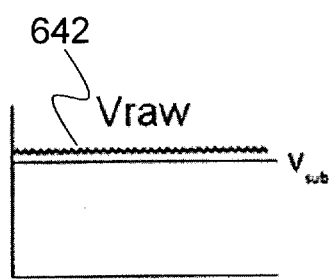
FIGS. 16A, 16B and 16C are graphical illustrations of signals used in the process of obtaining a direct current (DC) component of the PPG signal, according to an exemplary embodiment.
Figure 16B:
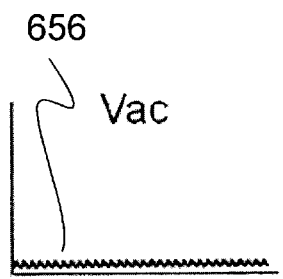
Figure 16C:
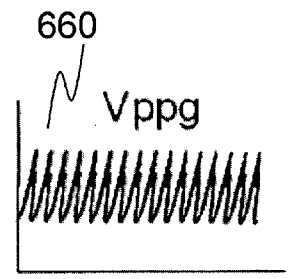
Figure 17:
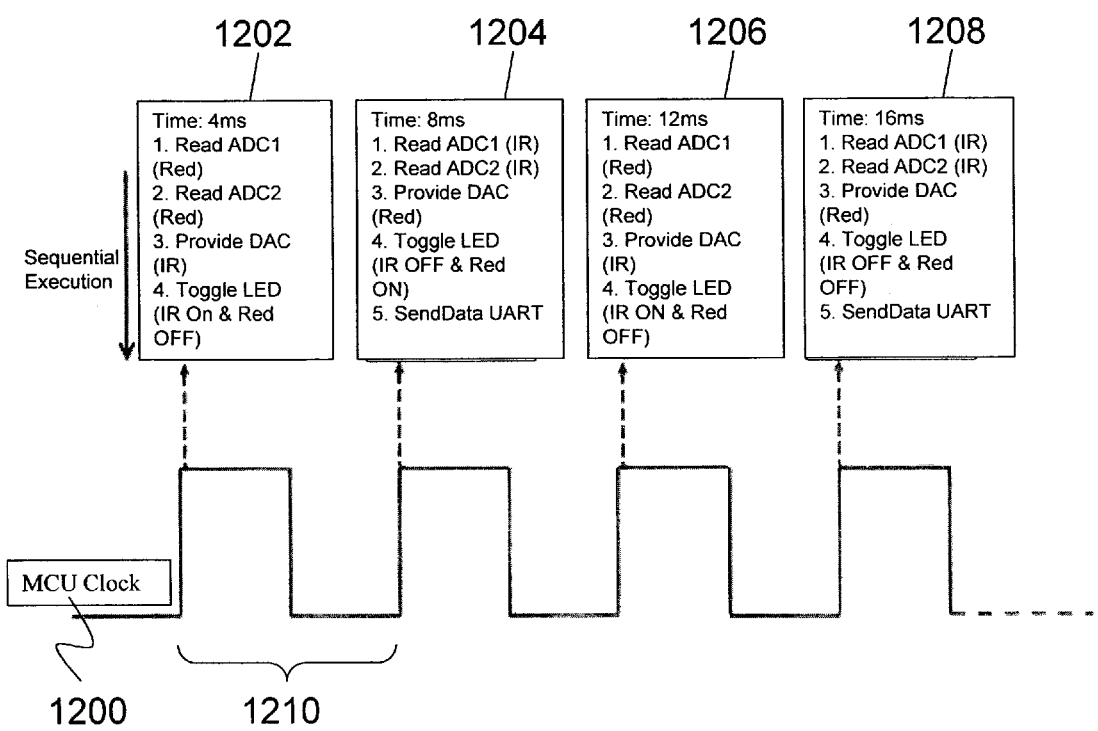
FIG. 17 is an illustration of a sequence of data collection performed during the process of obtaining the PPG signal, according to an exemplary embodiment.

The resolution of the new raw signal 660 is thus enhanced substantially when digitized at ADC2 662, as can be seen from the graphical representations of the Vraw signal 642 in FIG. 16A, Vac 656 in FIG. 16B, and Vppg 660 in FIG. 16C.

Referring to FIG. 11, in order to collect the data, an MCU clock 1200 is set to toggle at a predetermined interval to accommodate retrieving results from both LED(IR) 664 and LED(RED) 666 during a respective first interval 1202 and second interval 1204. In the non-limiting embodiment shown in FIG. 11, the interval 1210 is set to 4 milliseconds. The data collection sequence is then repeated in the third interval 1206 and fourth interval 1208. Before each toggle between the two LEDs, data from ADC1 644 and ADC2 662 are taken and sent to UART.

Figure 18:
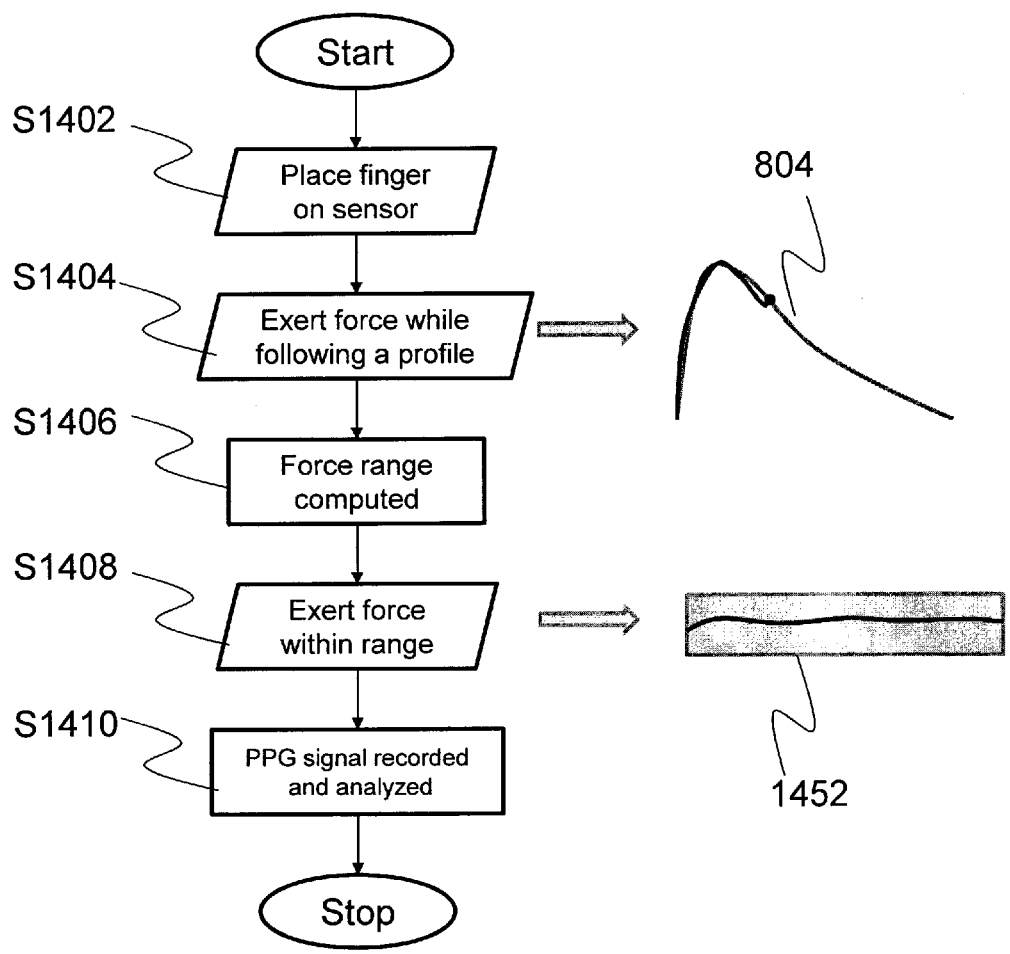
FIG. 18 is a flow chart illustrating a method of measuring the PPG signal on a sensing device using feedback from the pressure detection assembly, according to an exemplary embodiment.
Figure 19:
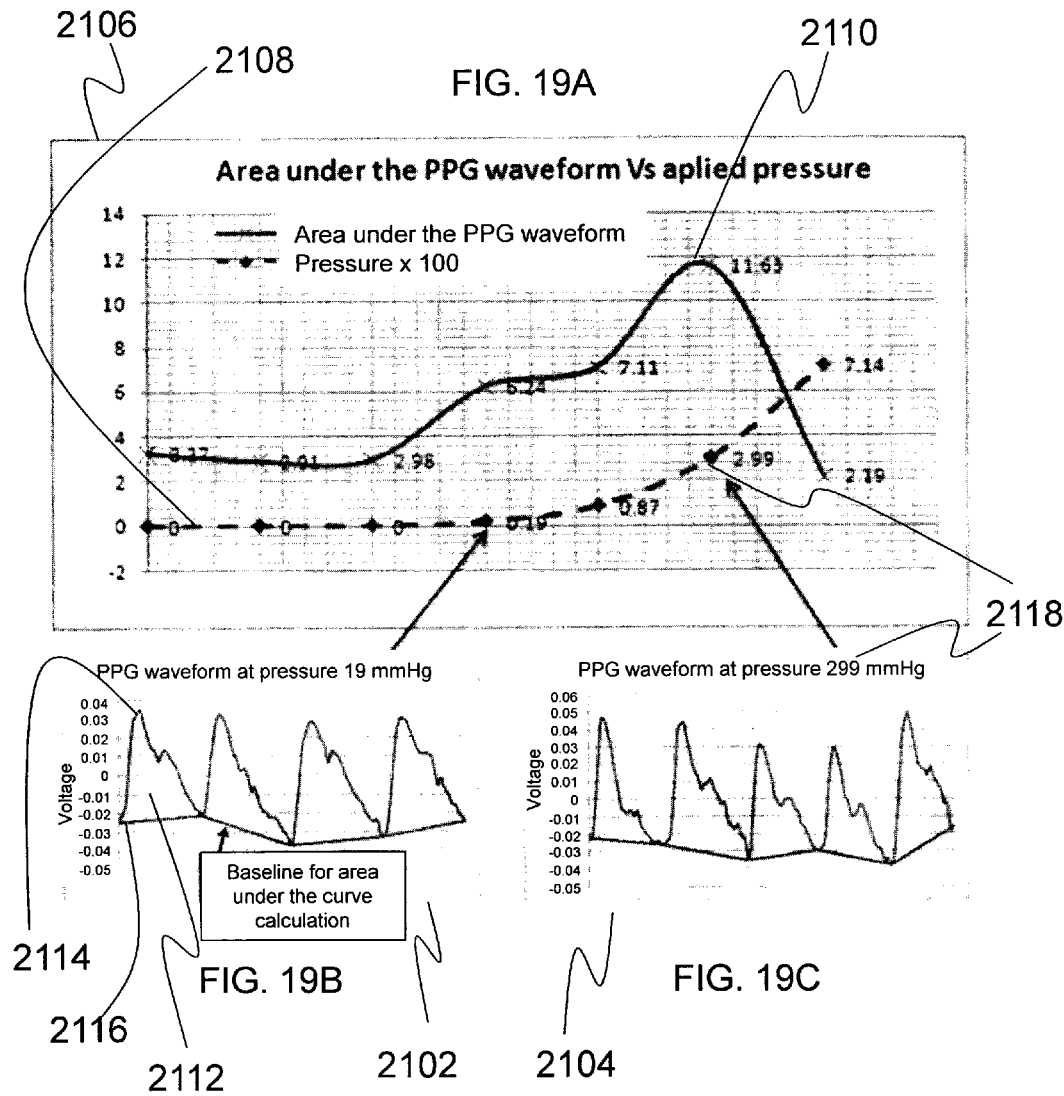
FIGS. 19A, 19B and 19C are graphical representations of the correlation between a PPG waveform and an applied pressure, as would be used in the method of measuring an optimal PPG signal, according to an exemplary embodiment.

One exemplary embodiment of a method of using the sensing device is described herein with reference to FIG. 18, with a corresponding exemplary GUI illustrated in FIGS. 19A-19C. A user seeking to obtain his or her PPG signals will first place a body part, such as a finger, on the sensor surface of the sensing device (S1402). Calibration of the device to the individual user may be performed (S1404), where the user is asked to apply an amount of pressure over a specific period of time, corresponding to a force profile 804, (see FIG. 7). In other words, the user is asked to vary the applied pressure such that the system can determine an optimum pressure for the user by analyzing the resulting PPG waveforms that result from the variety of applied pressures (S1406). The user may also be presented with at least one measured PPG waveform generated by a particular amount of applied pressure, as illustrated in the graphical displays in FIGS. 19B and 19C. FIG. 19A is a graphical display 2106 which shows the relationship of a calculated area 2110 under the curve in FIGS. 19B and 19C with respect to applied pressure 2108. FIGS. 19B and 19C are graphical displays 2102 and 2104, respectively, which illustrate the different PPG waveforms at different applied pressures, and how the area under curve of the PPG waveform is computed. As shown in FIG. 19A, the optimum pressure 2118 applied in FIG. 19C, 299 mmHg, corresponds to the largest area 2110 of PPG waveform detected during the calibration (S1404). Once this optimum pressure is determined, a subsequent measurement period begins, during which the user is asked to apply pressure within an optimum range above and below the optimum pressure (S1408). As previously described with regard to FIG. 8A, the amount of pressure being applied by the user may be displayed in a graph 618 on the display 614 so that the user can see the amount of pressure being applied in real-time. The graph 618 may also be displayed using the pressure status bar 620. If the amount of force being applied by the user falls outside of the optimum range, the system can detect this in real-time and will ask the user to increase or decrease the applied pressure in order to remain within the range of optimum pressure and record the best possible PPG signal quality (S1410).

Optimum pressure is determined as the pressure at which the measured PPG signal has the largest waveform amplitude, or area 2112 under the PPG waveform, as shown in FIG. 19B by the area 2112 bounded by the PPG signal 2114 and baseline 2116. FIG. 19A then graphs the variation of the area 2112 under the PPG waveform with respect to the pressure 2108 applied on the sensor. As may be observed in this example, the optimum pressure 2118 is at 299 mmHg, where area 2112 under the curve is at its maximum of 11.63.

Figure 20:
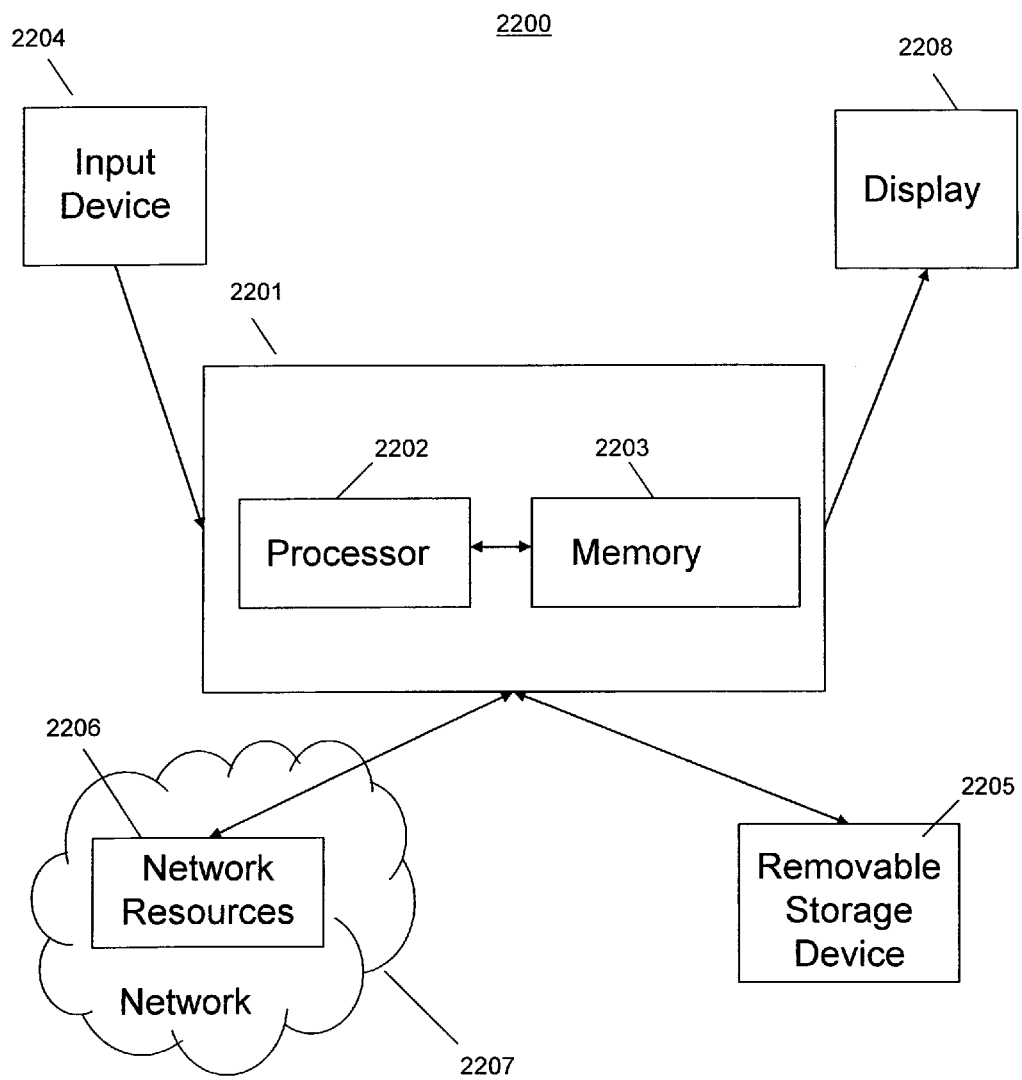
FIG. 20 is a block diagram of a computer system upon which the device and methods may be implemented, according to an exemplary embodiment.

FIG. 20 is a block diagram that illustrates an embodiment of a computer/server system 2200 upon which an embodiment of the inventive methodology may be implemented. The system 2200 includes a computer/server platform 2201 including a processor 2202 and memory 2203 which operate to execute instructions, as known to one of skill in the art. The term "computer-readable medium" as used herein refers to any medium that participates in providing instructions to processor 2202 for execution. Additionally, the computer platform 2201 receives input from a plurality of input devices 2204, such as a keyboard, mouse, touch device or verbal command. The computer platform 2201 may additionally be connected to a removable storage device 2205, such as a portable hard drive, optical media (CD or DVD), disk media or any other medium from which a computer can read executable code. The computer platform may further be connected to network resources 2206 which connect to the Internet or other components of a local public or private network. The network resources 2206 may provide instructions and data to the computer platform from a remote location on a network 2207. The connections to the network resources 2206 may be via wireless protocols, such as the 802.11 standards, Bluetooth® or cellular protocols, or via physical transmission media, such as cables or fiber optics. The network resources may include storage devices for storing data and executable instructions at a location separate from the computer platform 2201. The computer interacts with a display 2208 to output data and other information to a user, as well as to request additional instructions and input from the user. The display 2208 may therefore further act as an input device 2204 for interacting with a user.

APPLICATIONS

The sensing device disclosed herein is an effective tool for acquiring PPG signals as well as detect the optimum force required by the user to produce PPG signal of desirable quality. As the sensing device is capable of functioning with only one wave emitter and one wave detector, the sensing device may be advantageously compacted into a substantially small volume for efficient user portability. In addition, the sensing device disclosed herein has minimal components but yet still able to detect reflected light signals as well as the compressive force exerted by the user.

Due to the strategic positioning of the force transmitting member, the force transmitting member substantially prevents waves emitted from the wave emitter to travel directly to the wave detector to reduce noise in the detected signal, without the need of an additional shading/shielding component.

It will be appreciated by a person skilled in the art that other variations and/or modifications may be made to the specific embodiments without departing from the spirit or scope of the invention as broadly described. The present embodiments are, therefore, to be considered in all respects to be illustrative and not restrictive.

The invention claimed is:

1. A sensing device comprising:
an electromagnetic wave emitter for emitting electromagnetic waves to a surface;
an electromagnetic wave detector for detecting the emitted electromagnetic waves that are reflected from the surface;
a force transmitting member configured to transmit a force applied thereto for detection,
wherein the force transmitting member is positioned relative to the electromagnetic wave emitter and electromagnetic wave detector to substantially prevent waves emitted by the electromagnetic wave emitter from travelling directly to the electromagnetic wave detector;
a force detector coupled to the force transmitting member for detecting the force transmitted by the force transmitting member; and
a feedback unit coupled to the force detector, the feedback unit being configured to correlate the quality of the detected electromagnetic wave with the amount of force applied to the force transmitting member and provide feedback related to the correlation by:
computing an area under waveforms of detected signals corresponding to a variety of applied pressure amounts, and
determining an optimum pressure to correspond a largest computed area, from the variety of applied pressure amount.

2. The sensing device of claim 1, wherein the force transmitting member is disposed between the electromagnetic wave emitter and electromagnetic wave detector.

3. The sensing device of claim 1, wherein the force detector comprises a microelectromechanical system (MEMs).

4. The sensing device of claim 1, wherein the force detector comprises a piezo-based sensor.

5. The sensing device of claim 4, wherein the piezo-based sensor is selected from a group consisting of a piezoelectric based sensor, a piezoresistive based sensor, and a piezocapacitive based sensor.

6. The sensing device of claim 4, wherein the piezo-based sensor is provided as a flexible printed circuit.

7. The sensing device of claim 1, wherein the electromagnetic wave emitter comprises a light emitting diode.

8. The sensing device of claim 7, wherein the electromagnetic wave detector comprises a photo detector.

9. The sensing device of claim 1, wherein the surface comprises a surface portion of a user for measurement.

10. The sensing device of claim 1, wherein the force transmitting member is elongate in shape.

11. The sensing device of claim 1, wherein the electromagnetic wave emitter and electromagnetic wave detector are disposed on substantially the same plane.

12. The sensing device of claim 11, wherein the electromagnetic wave emitter and electromagnetic wave detector are disposed on a same substrate.

13. The sensing device of claim 1, wherein the sensing device is capable of detecting photoplethysmography signals.

14. The sensing device of claim 1, further comprising:
a housing for housing the electromagnetic wave emitter, electromagnetic wave detector and force transmitting member, wherein the housing is adapted to provide structural rigidity to the sensing device.

15. A method for preparing a sensing device comprising:
providing an electromagnetic wave emitter for emitting electromagnetic waves to a surface;
providing an electromagnetic wave detector for detecting the emitted electromagnetic waves that are reflected from the surface;
positioning a force transmitting member relative to the electromagnetic wave emitter and electromagnetic wave detector to substantially prevent electromagnetic waves emitted by the electromagnetic wave emitter from travelling directly to the wave detector,
wherein the force transmitting member is configured to transmit a force applied thereto for detection;
coupling a force detector to the force transmitting member for detecting the force transmitted by the force transmitting member; and
coupling a feedback unit to the force detector, the feedback unit being configured to correlate the quality of the detected electromagnetic wave with the amount of force applied to the force transmitting member and provide feedback related to the correlation by:
computing an area under waveforms of detected signals corresponding to a variety of applied pressure amounts, and
determining an optimum pressure to correspond a largest computed area, from the variety of applied pressure amount.

16. A personal mobile sensing (PMS) system comprising:
a sensing device comprising:
- an electromagnetic wave emitter for emitting electromagnetic waves to a surface;
- an electromagnetic wave detector for detecting the emitted electromagnetic waves that are reflected from the surface;
- a force transmitting member configured to transmit a force applied thereto for detection, wherein the force transmitting member is positioned relative to the electromagnetic wave emitter and electromagnetic wave detector to substantially prevent electromagnetic waves emitted by the electromagnetic wave emitter from travelling directly to the wave detector;
- a force detector coupled to the force transmitting member for detecting the force transmitted by the force transmitting member; and
- a personal mobile processing device for coupling to the sensing device to process a signal obtained from said sensing device, the personal mobile processing device comprising:
  - a feedback unit coupled to the force detector, the feedback unit being configured to correlate the quality of the detected electromagnetic wave with the amount of force applied to the force transmitting member and provide feedback related to the correlation by:
    - computing an area under waveforms of detected signals corresponding to a variety of applied pressure amounts, and
    - determining an optimum pressure to correspond a largest computed area, from the variety of applied pressure amount.

17. The PMS system of claim 16, wherein the force transmitting member is disposed between the electromagnetic wave emitter and electromagnetic wave detector.

18. The PMS system of claim 16, wherein the force detector comprises a microelectromechanical system (MEMs).

19. The PMS system of claim 16, wherein the force detector comprises a piezo-based sensor.

20. The PMS system of claim 19, wherein the piezo-based sensor is selected from a group consisting of a piezoelectric based sensor, a piezoresistive based sensor, and a piezocapacitive based sensor.

21. The PMS system of claim 16, wherein the surface comprises a surface portion of a user for measurement.

22. The PMS system of claim 16, wherein the electromagnetic wave emitter and electromagnetic wave detector are disposed on substantially the same plane.

23. The PMS system of claim 16, wherein the sensing device is capable of detecting photoplethysmography signals.

24. The PMS system of claim 16, wherein the sensing device is coupled to the personal mobile processing device in a cableless configuration.

* * * * *